(12) United States Patent
Shevitz

(10) Patent No.: US 11,141,578 B2
(45) Date of Patent: Oct. 12, 2021

(54) DEVICE FOR ASEPTICALLY CONNECTING LARGE BORE TUBING

(71) Applicant: Jerry Shevitz, Livingston, NJ (US)

(72) Inventor: Jerry Shevitz, Livingston, NJ (US)

(*) Notice: Subject to any disclaimer, the term of this patent is extended or adjusted under 35 U.S.C. 154(b) by 253 days.

(21) Appl. No.: 16/305,798

(22) PCT Filed: May 30, 2017

(86) PCT No.: PCT/US2017/034947
§ 371 (c)(1),
(2) Date: Nov. 29, 2018

(87) PCT Pub. No.: WO2017/210161
PCT Pub. Date: Dec. 7, 2017

(65) Prior Publication Data
US 2019/0167971 A1     Jun. 6, 2019

Related U.S. Application Data

(60) Provisional application No. 62/344,079, filed on Jun. 1, 2016.

(51) Int. Cl.
*A61M 39/18* (2006.01)
*A61M 39/12* (2006.01)
*A61M 39/10* (2006.01)
*F16L 29/00* (2006.01)
*F16L 23/02* (2006.01)
*F16L 23/024* (2006.01)

(52) U.S. Cl.
CPC ......... *A61M 39/18* (2013.01); *A61M 39/10* (2013.01); *A61M 39/12* (2013.01); *F16L 23/02* (2013.01); *F16L 29/007* (2013.01); *F16L 23/024* (2013.01); *F16L 2201/44* (2013.01)

(58) Field of Classification Search
CPC ...... A61M 39/10; A61M 39/12; A61M 39/18; F16L 23/02; F16L 23/024; F16L 23/028; F16L 23/0283; F16L 23/0286
See application file for complete search history.

(56) References Cited

U.S. PATENT DOCUMENTS

| | | | |
|---|---|---|---|
| 1,643,597 A | 9/1927 | Anglada | |
| 2,831,708 A * | 4/1958 | Kircher | F16L 23/028 285/31 |
| 4,187,846 A | 2/1980 | Lolachi | |
| 6,299,216 B1 * | 10/2001 | Thompson | F16L 23/167 285/93 |
| 6,679,529 B2 | 1/2004 | Johnson | |
| 7,523,918 B2 | 4/2009 | Maltkovitch | |
| (Continued) | | | |

FOREIGN PATENT DOCUMENTS

| GB | 2506148 | 3/2014 |
|---|---|---|
| WO | WO 2013/147688 | 10/2013 |

*Primary Examiner* — Nathan R Price
*Assistant Examiner* — Courtney B Fredrickson
(74) *Attorney, Agent, or Firm* — Law Firm of Allan Fried; Allan H. Fried

(57) ABSTRACT

A connector for facilitating the connection of one piece of tubing to another so that fluid can flow from one piece to the other in a sterile manner. Characteristics of the connector include, but are not limited to, a flange at one of the connector, the flange comprising a recess for storage of at least part of a protective shield which Is removable after the flange is connected to the flange of a second connector.

16 Claims, 33 Drawing Sheets

(56) References Cited

U.S. PATENT DOCUMENTS

| | | |
|---|---|---|
| 7,631,660 B2 | 12/2009 | DeCler |
| 7,678,096 B2 | 3/2010 | Biddel |
| 7,918,243 B2 | 4/2011 | Diodati |
| 7,922,211 B2 | 4/2011 | Arthun |
| 8,029,023 B2 | 10/2011 | Arthun |
| 8,491,016 B2 | 7/2013 | Williams |
| 8,596,326 B2 | 12/2013 | Loy |
| 2003/0030272 A1 | 2/2003 | Johnson |
| 2006/0252298 A1* | 11/2006 | Biddel ............ A61M 39/18 439/405 |
| 2009/0050213 A1* | 2/2009 | Biddell ........... A61M 39/18 137/15.01 |
| 2010/0032941 A1* | 2/2010 | Cabezas .......... F16L 23/026 285/55 |
| 2013/0207380 A1 | 8/2013 | Wiliams |
| 2015/0028586 A1 | 1/2015 | Gerst |
| 2015/0061282 A1* | 3/2015 | Faldt ............. A61M 39/105 285/124.5 |
| 2015/0130180 A1* | 5/2015 | Fontenot ......... F16L 23/003 285/15 |
| 2015/0344161 A1 | 12/2015 | Selker |
| 2017/0284584 A1* | 10/2017 | Kesselaar ........ F16L 37/113 |

\* cited by examiner

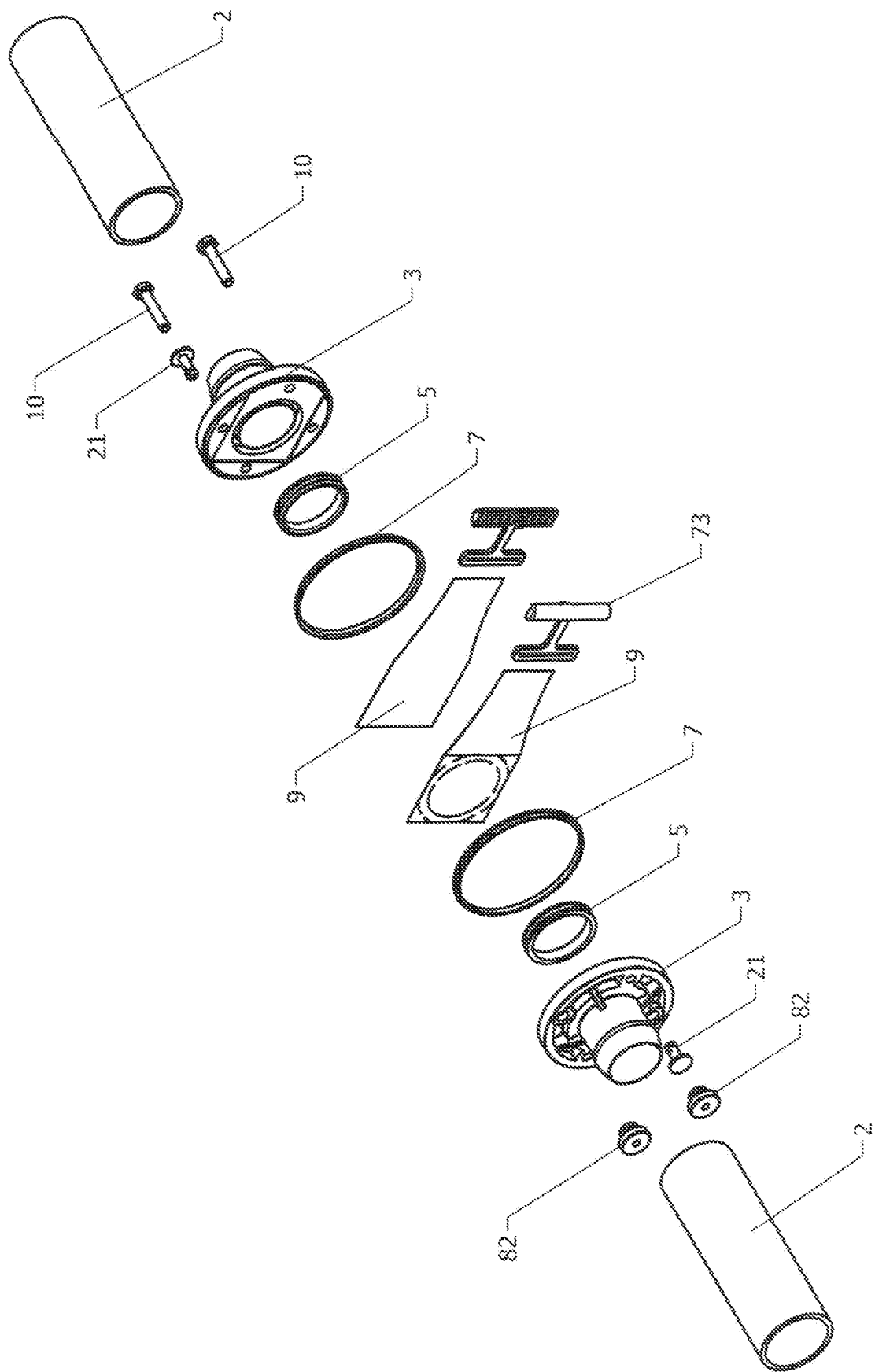

DEVICE FOR ASEPTICALLY CONNECTING LARGE BORE TUBING

CROSS REFERENCE TO RELATED APPLICATIONS

This application claims the benefit of U.S. provisional application No. 62/344,079 filed Jun. 1, 2016, which application is incorporated by reference in its entirety herein.

FIELD OF THE INVENTION

The field of the invention is aseptically shielded connector devices that can be joined in an aseptic manner and used to join tubing that conveys fluid from one place to another.

BACKGROUND OF THE INVENTION

In processing biological materials, there is frequently a need to move large volumes of fluids efficiently and at reasonably low shear rates so as not to damage frail, high value products. Increasing the inner diameter of the tubing is a way to achieve those goals. The current invention is designed to address these objectives.

The means for making aseptic connections between tubings is to some extent well understood and well developed. In the past such connections may have involved treating the connecting ends with a bactericidal agent, flaming or attaching the ends in a biological safety hood. The use of such methods; however, is fraught with problems. Bactericidal agents include antibiotics or other chemicals that inactivate contaminating microorganisms. Antibiotics are expensive and frequently undesired or not permitted in a particular process. Bactericidal agents, can also be toxic or may contaminate the process. The use of a flame to sterilize equipment was used routinely in the past but is no longer permissible because it creates a fire hazard. A biological safety hood, although an effective place to work, is a fixture and frequently not accessible at the work site.

The introduction of steam to the process facility revolutionized the ability to perform the necessary operations required in a manufacturing facility. Although steam is a versatile method for sterilizing components, it requires an infrastructure, including a steam generation capability. It also requires a means of transporting, via piping, the steam to where it is needed. In addition, the associated infrastructure must be rated to accommodate live steam at high pressure and temperatures. In addition, it requires components that manage and control live steam flow. Such components can be very costly. Therefore, a steam sterilization capability is typically limited to large facilities. Furthermore, to accommodate steam, most processes involve stainless steel or other materials that are compatible with steam. However, not all components used in processing are resistant to heat sterilization; e.g., probes, sensors, single-use vessels, and accessories.

In the past two decades, advancements in biotechnology and bioprocessing have led to changes in bioprocessing requirements. Many of these changes are occurring in smaller biotechnology companies rather than in large pharmaceutical companies. Without the development of new technology, smaller companies would typically not have the resources or facilities to produce products for testing and trials. However, even large companies found it difficult and costly to expand facilities on the basis of previous technologies. As a result, alternate methods of manufacturing that alleviated some of the problems of stainless steel based technologies were developed.

Some of the new methods include new vessel construction. These vessels incorporate synthetic materials rather than stainless steel. In most cases, pliable materials in the form of "bags" or liners are used. Such containers are relatively inexpensive compared to stainless steel. Also, such bags or liners need only be used once; following a single use, the bag or liner may be disposed of. Unlike stainless steel, no cleaning or cleaning validation is required by the user. Handling or using such "bags" is substantially more manageable than using large stainless steel vessels and skids. Additionally, single-use synthetic vessels are supplied precertified for their intended use; there is no or minimal need to clean or recertificy the process vessel prior to use. A user can purchase a single-use production vessel when needed, thereby avoiding overhead required to prepare and manage the vessel.

Along with developments in the equipment for culturing cells, methods for growing and processing cell cultures, particularly those of mammalian cells, have also undergone major changes. The process of continuous culturing has become more acceptable and common than batch culturing. The primary difference between batch and continuous culturing is that, in the former, scale-up is achieved by using progressively larger vessels; in the latter, scale-up is achieved largely by maintaining the culture for longer duration by removing waste products and supplying fresh nutrients. Such continuous culturing achieves higher growth characteristics and higher product output compared to batch culturing. The use of continuous culturing in combination with single-use vessels has brought within reach the capacity to produce the required quantities of products, by even small companies, and has facilitated the ability to bring new and novel drugs to market.

A secondary service industry has evolved alongside the change in vessels and manufacturing methods. The present invention focuses is on one aspect of those developments: on how to connect in a sterile mannerflow paths, conduits, instruments, other equipment, processing vessels and other accessories to each other. More specifically, the invention addresses methods for connecting large-bore tubing reliably and in a sterile manner.

Current methods for making sterile connectors between adjacent segments of tubing are best suited to tubing with an inner diameter ("ID") between 0.125 inches and 1.25 inches. U.S. patents of interest include, but are not necessarily limited to: U.S. Pat. Nos. 6,679,529; 6,880,801; 6,655,655; 7,678:096; 8,491,016; 8,899,267 and 9,027,968.

The prior art does include shieldable flanged connectors that can be enhanced with a removable shield that blocks the central opening of the connector tube until the connector is ready to be joined to another connector. However, those connectors are not well-suited for tubes with an inner diameter of 1.5 inches or more. Connectors of the present invention build upon a prior art shieldable flanged connector design-a connector tube surrounded at one end by both a flange and an O-ring attached to the flange—and include inventive features that are well-suited for such large bore tubing:

1) The rivets and screws that keep the flanges of two connectors flat against each other are positioned away from the flange peripheral rims and closer to the central axis of the connectors, a feature that reduces the distance between the pressure source in the connector center tube and the fasteners; this feature in turn reduces the area upon which the pressure may act compared to an equivalent connector that is fastened at the periphery. A pair of such flanged connectors, when joined to each other, are able to withstand greater pressures emanating from the fluid flowing through them. Another reason for adapting the flange connector is its scalability robustness; i.e., a connection between tubes of increased size is achieved by a proportional increase in the number of fasteners.

2) A recess in the flange acts as a compartment for storing most or all of a foldable protective shield; and
3) A V-ring at the outer perimeter of the flange provides, in relation to the O-ring, a second ring of protection against microbial contamination; and
4) The protective shield is enhanced with a pull grip that can be gripped with one's fingers and the palm of the hand, allowing greater pulling force to remove a shield sandwiched between the gaskets of two connectors.

Minor changes in the design can transform the genderless version of the connector to a gendered version.

BRIEF DESCRIPTION OF THE DRAWINGS

FIG. 1B is an exploded view of an example of a pair of four-fastener hole shielded connectors of the invention to be joined together and tubing. The area between the dashed lines on the shield 9 define an adhesive bonding area 63 on the side of the shield viewable in the figure.

BRIEF SUMMARY OF THE INVENTION

Figure 1A:
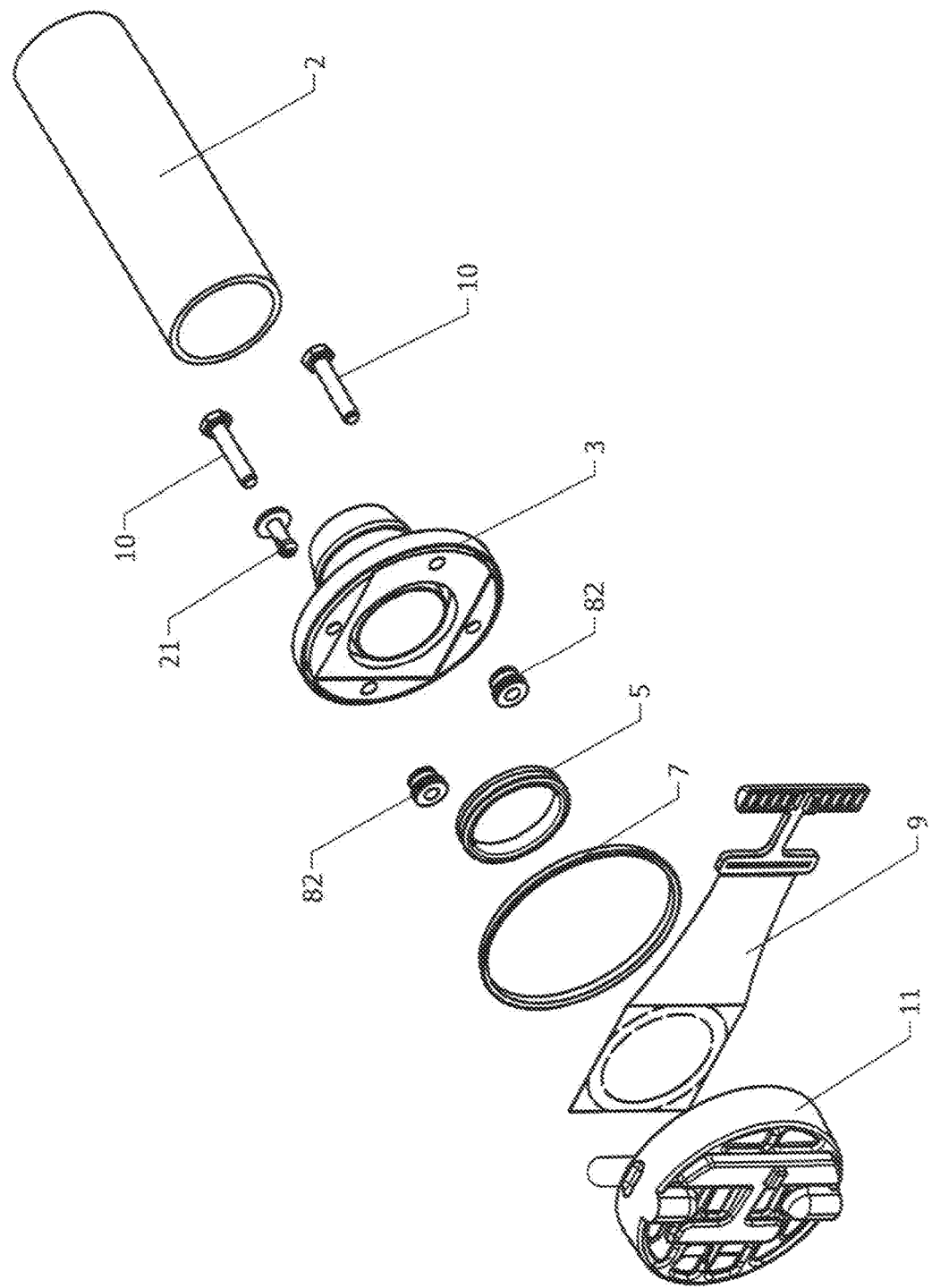
FIG. 1A is an exploded view of an example of a four fastener holed shielded connector of the invention, its face cap, and tubing. The area between the dashed lines on the shield 9 define an adhesive bonding area 63 on the side of the shield not viewable in the figure.

The invention is a flanged tubing connector enhanced with a protective shield covering its central channel. That connector can be joined to an identical or similar connector so that fluid can, in sterile fashion, flow from one piece of tubing, through both connectors, into a second piece of tubing. The design improves performance when large-bore tubing is being joined. One reason is that the rivets or bolts that connect opposing flanges in joined connectors are placed as far from the flange periphery or as close to the connected conduit and sealing gasket as reasonably possible—making the joined connectors more resistant to joint rupture or to deformation due to high fluid pressures.

In contrast to previous designs, each connector comprises an ample recess for storage of the protective shield thereby avoiding the necessity of dragging the shield across a tight-fitting abrasive flange surface while the shield is being removed from the joined connectors. Furthermore the shields are fitted with half of a T-shaped pull grip (combinable with the half from the joined connector) that accommodates all five fingers and the palm of a person's hand, allowing one to use nearly the full force of one's hand. The T-shaped pull grip makes it easier to pull the shield away from two joined connectors, a process that requires both breaking shield-to-flange adhesive bonds and pulling the shield through O-rings that are under compression forces. A protective cap with a compartment for internally storing the half pull grip is provided.

DETAILED DESCRIPTION

Terminology and Structure

The terminology is best understood initially by referring to the structures illustrated in the drawings. (Not all structures that contribute to the invention are discussed in this section.)

Figure 3A:
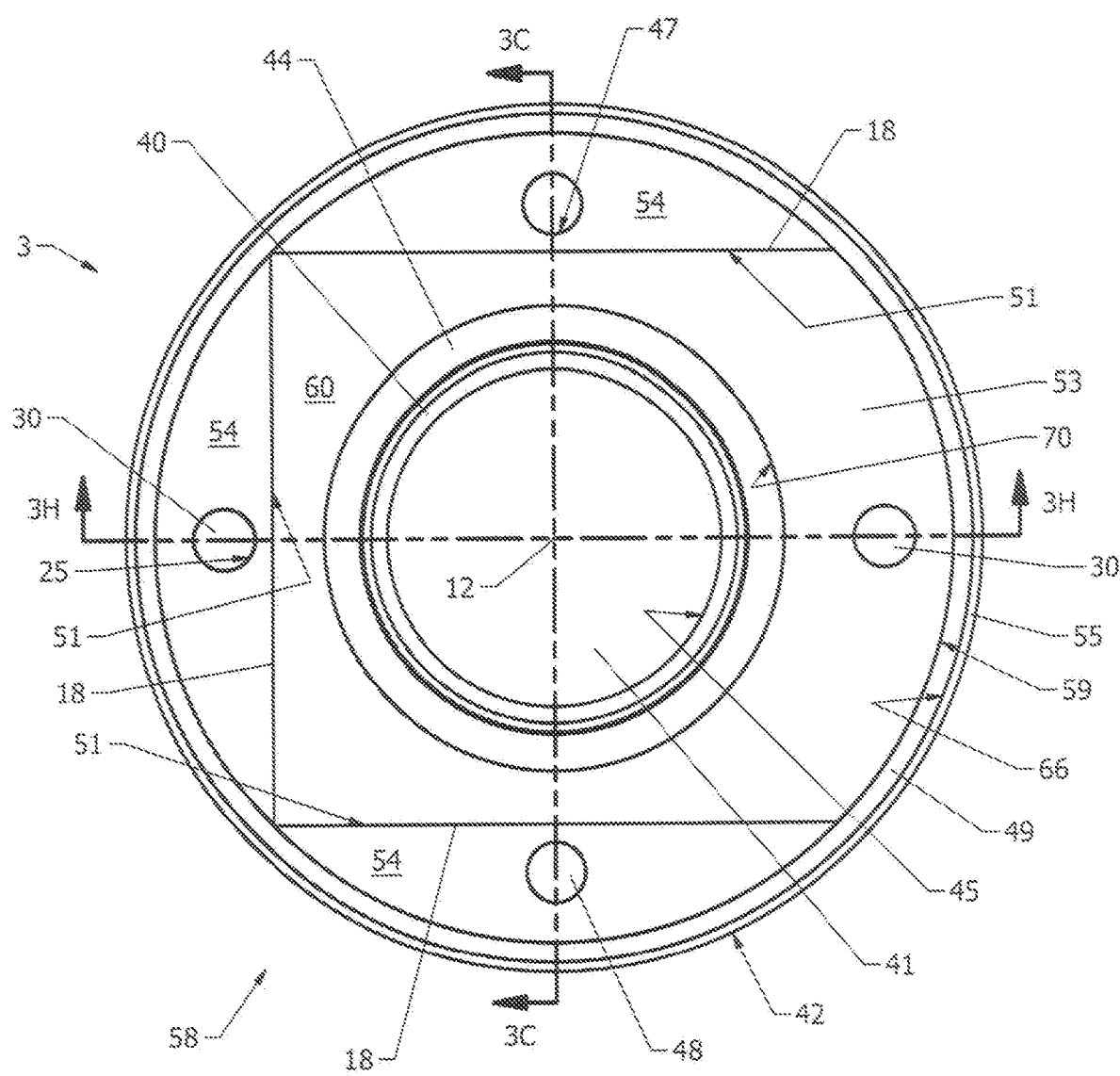
FIG. 3A is a front view of connector component 3 shown in FIG. 1A.
Figure 3B:
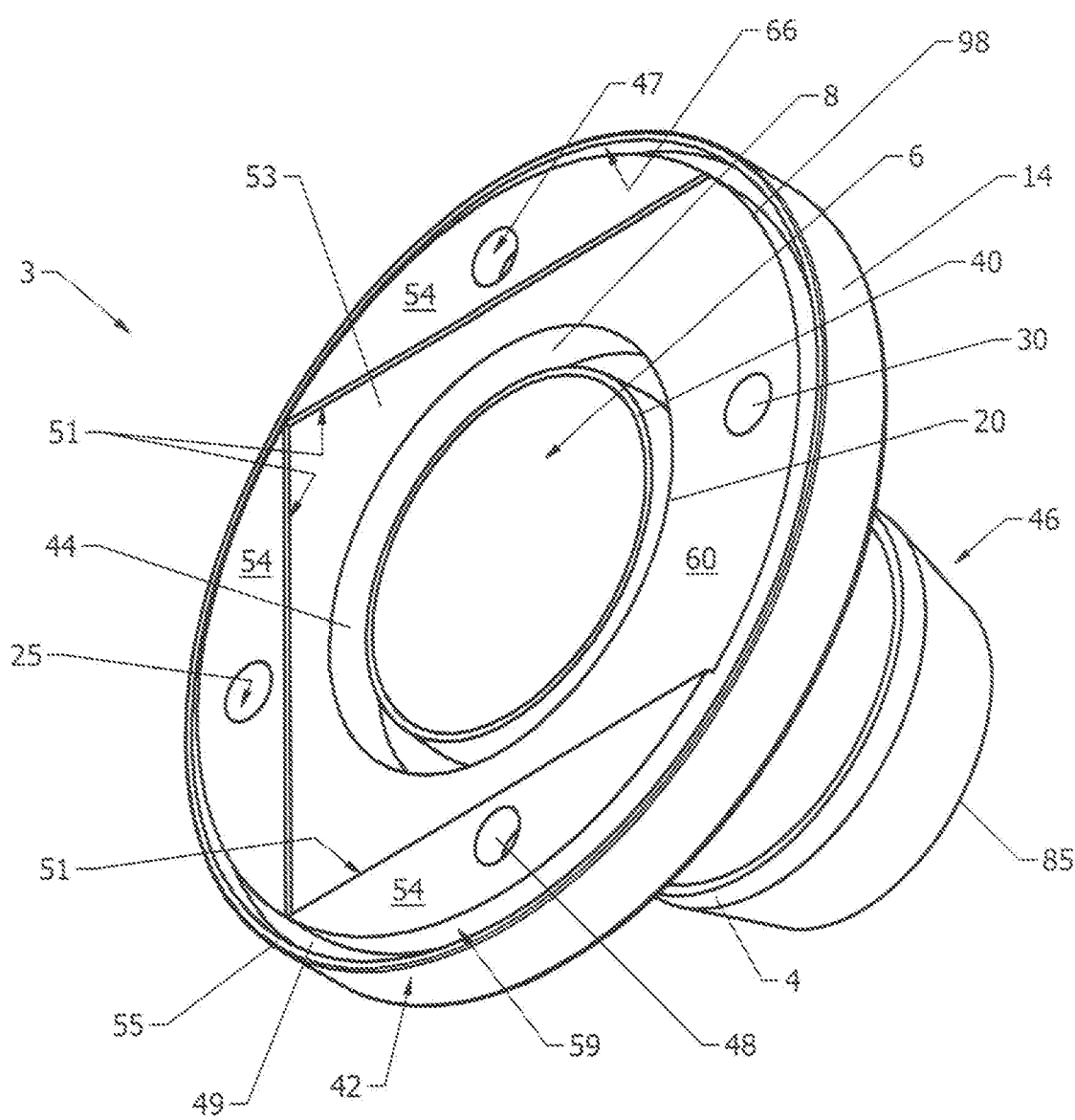
FIG. 3B is a perspective view of the front of the connector component shown in FIG. 3A.
Figure 3C:
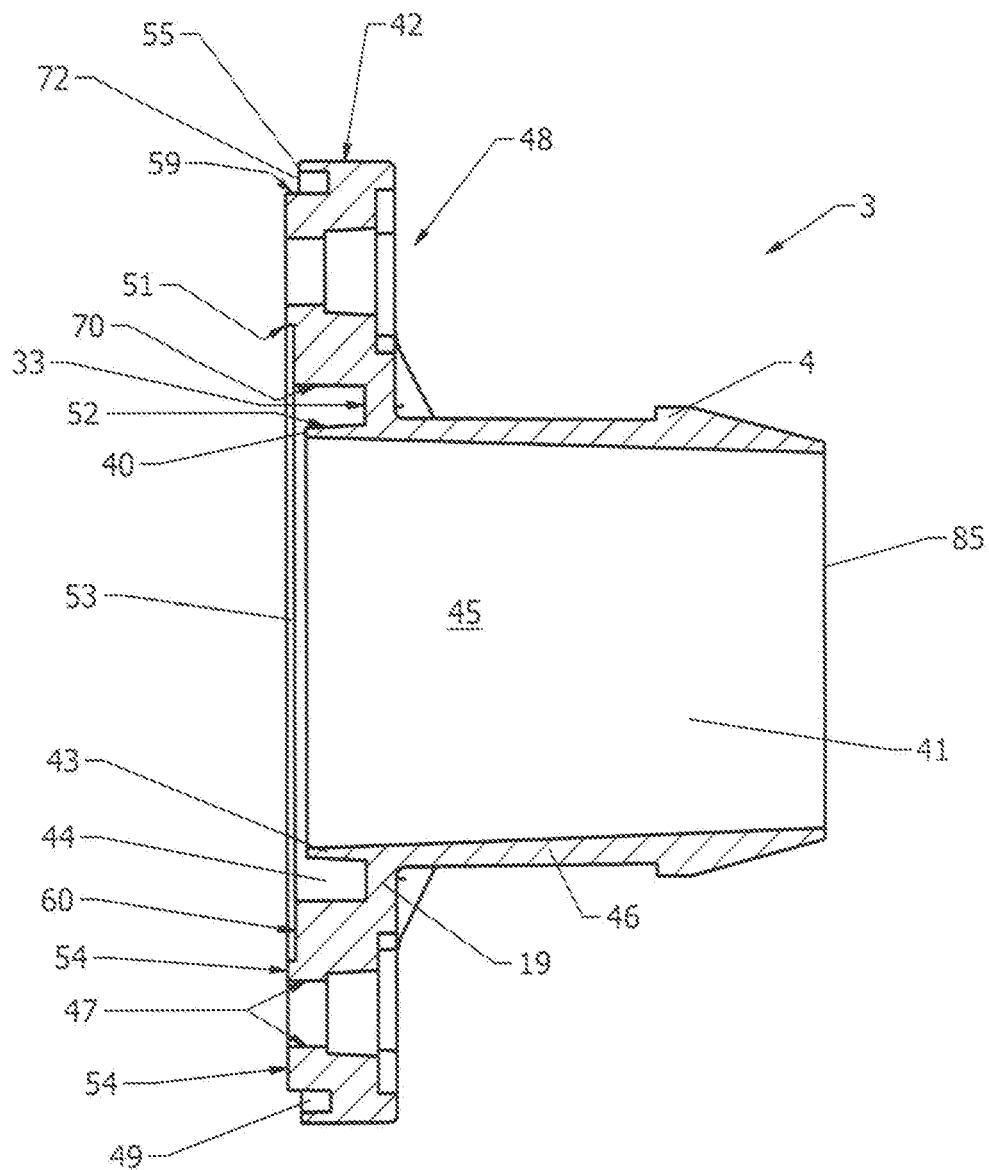
FIG. 3C is a sectional view of the connector component shown in FIG. 3A taken along the direction 3C-3C in FIG. 3A.
Figure 3D:
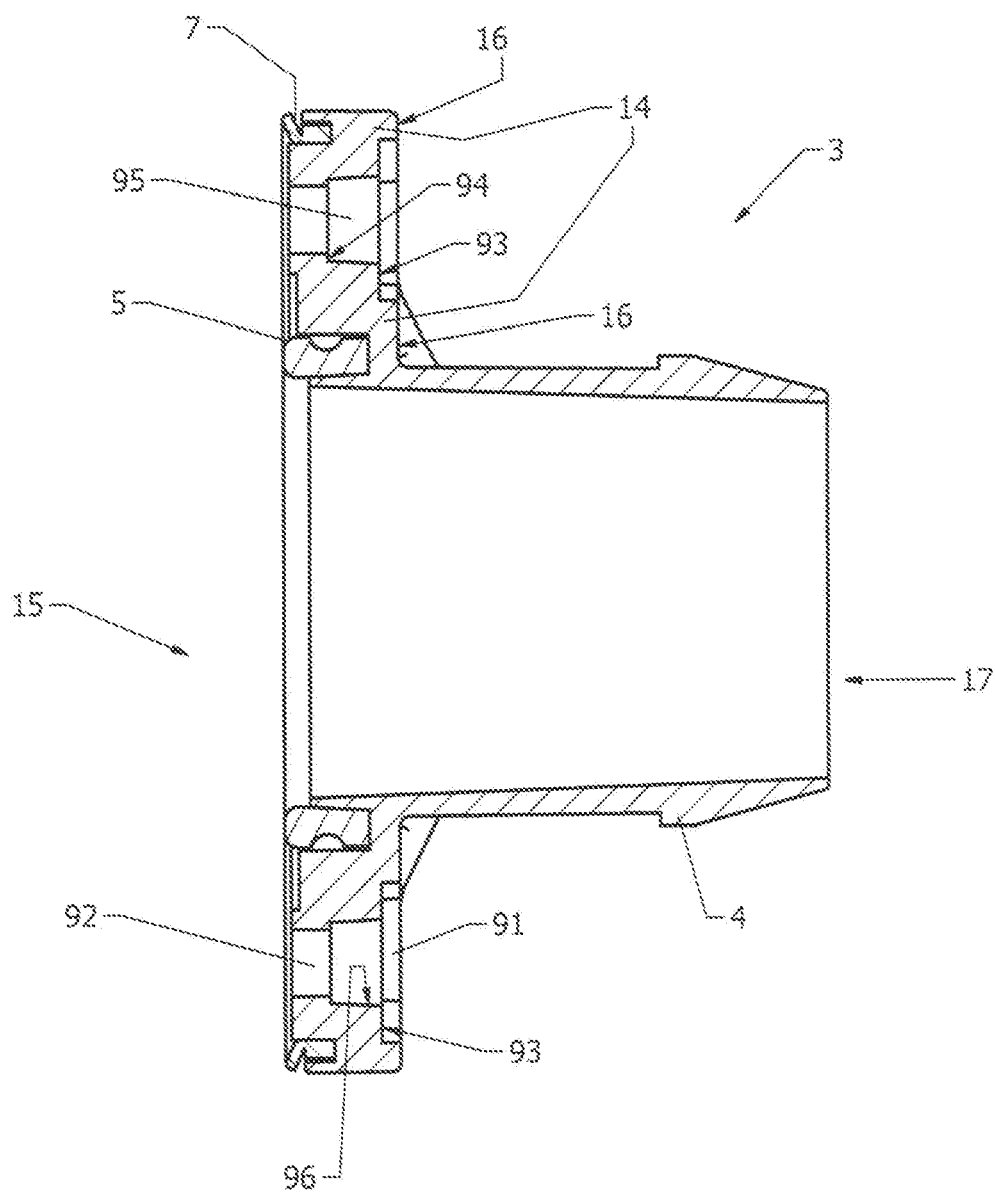
FIG. 3D is the sectional view shown in FIG. 3C but with the O-ring 5 and V-ring 7 shown.

Three major structures of the connector 3, shown in FIGS. 3C and 3D, are a connector tube 46 that forms the flow conduit; a hose barb 4 at one end of the tube 46; and a flange 14 at the other end of that tube. Also shown in the figures is a hose barb tube connector, although other tube connectors may be used, e.g., the sanitary "I" line type connector. The features of the flange 14 are described in greater detail below: The "proximal" end (defined by the connector tube proximal rim 40) of the connector tube is the end of the connector tube that is closest to the flange and indeed often encircled by the flange. The other end of the connector tube is the "distal" end 85. The proximal and distal ends of the connector tube are references for the use of the terms proximal and distal as to all components of the connector.

The proximal and distal ends of the connector tube are references for the use of the terms proximal and distal as to all components of the connector.

The "central axis" 12 of the connector tube 46 runs in a proximal to distal direction through the center of that tube. For two surfaces (or other items) that vary in their distance from the central axis, the surface closest to the central axis is the "more central" surface and the surface farthest from the central axis is the "peripheral" surface.

An "opening to a hole" is an opening in a surface where the hole appears.

Figure 3E:
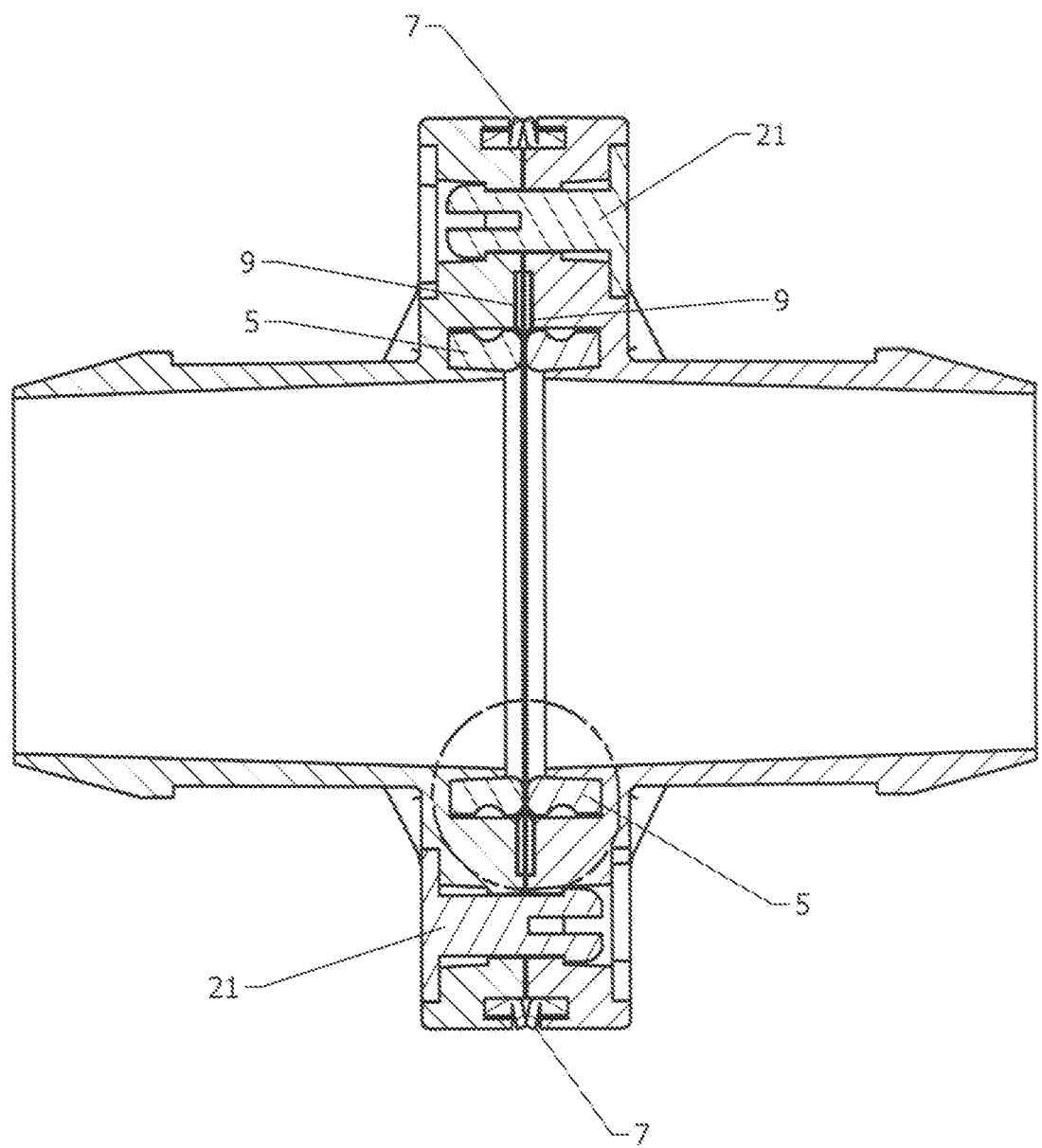
FIG. 3E is a sectional view of paired connector components with the structure described on FIGS. 1A-1B and 3A-3D, with two protective shields 9 being between the connector components.
Figure 3F:
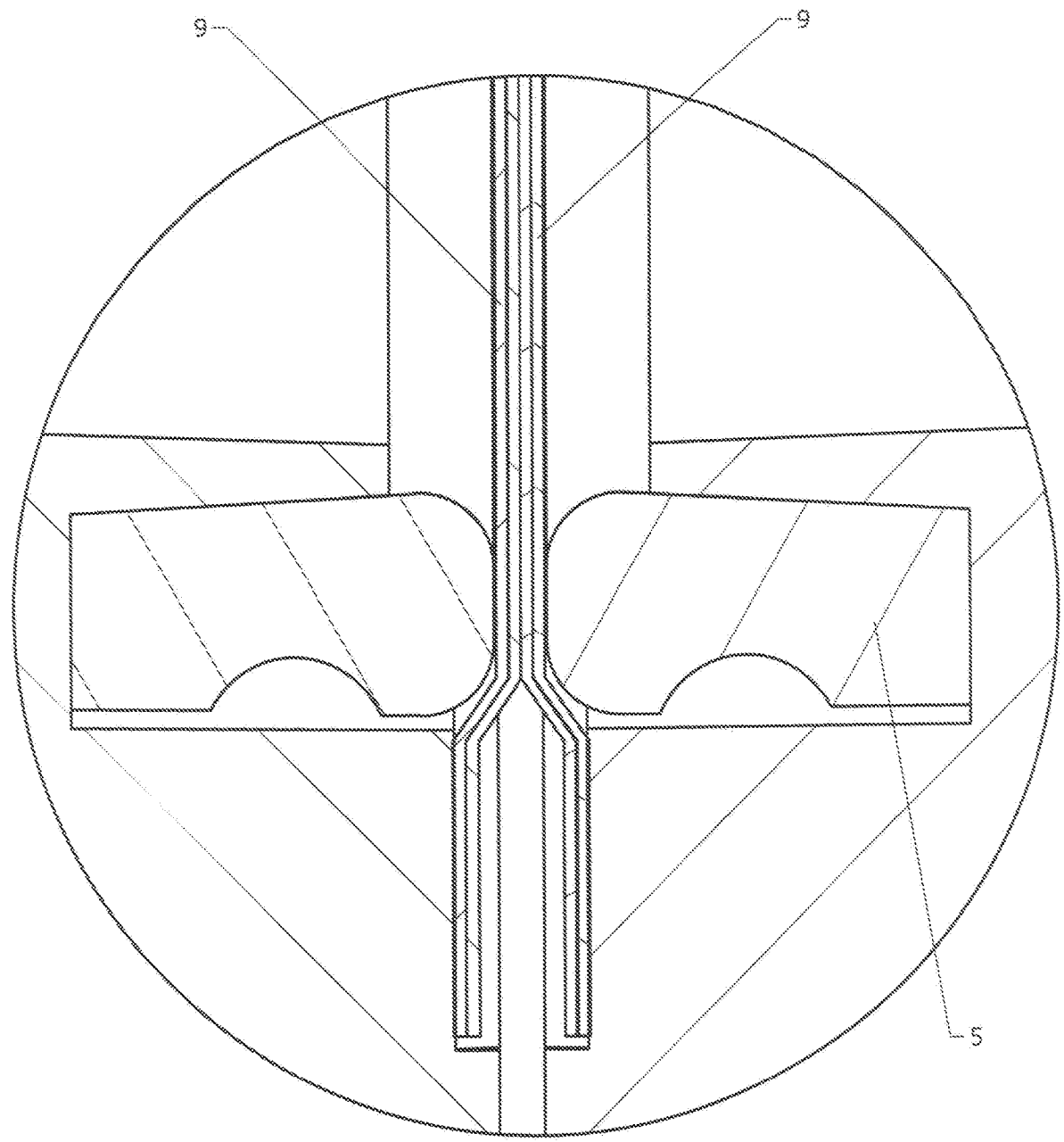
FIG. 3F is an enlarged view of the circled portion of FIG. 3E.
Figure 3G:
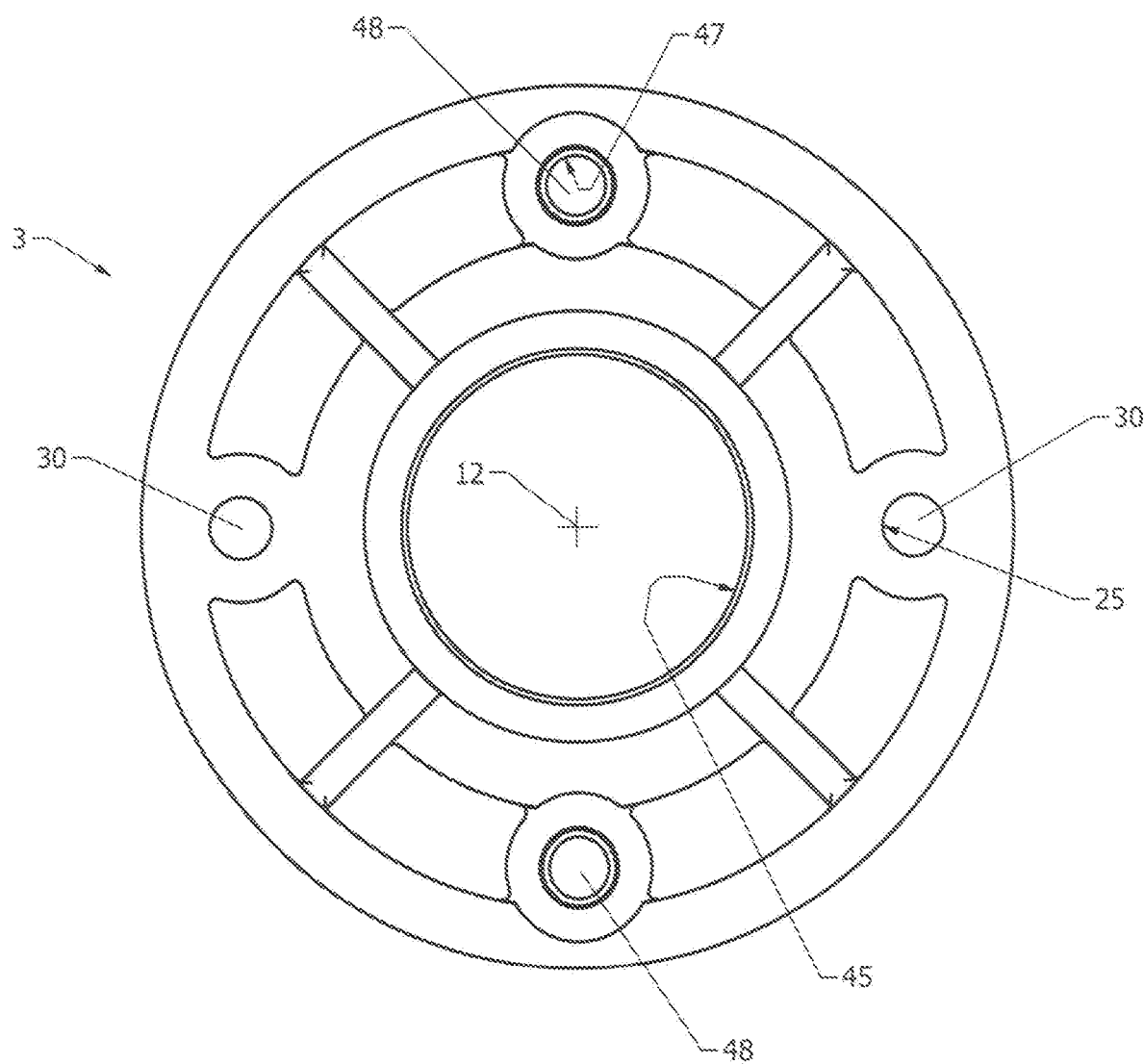
FIG. 3G is the back view of a connector component shown in FIG. 3A.
Figure 3H:
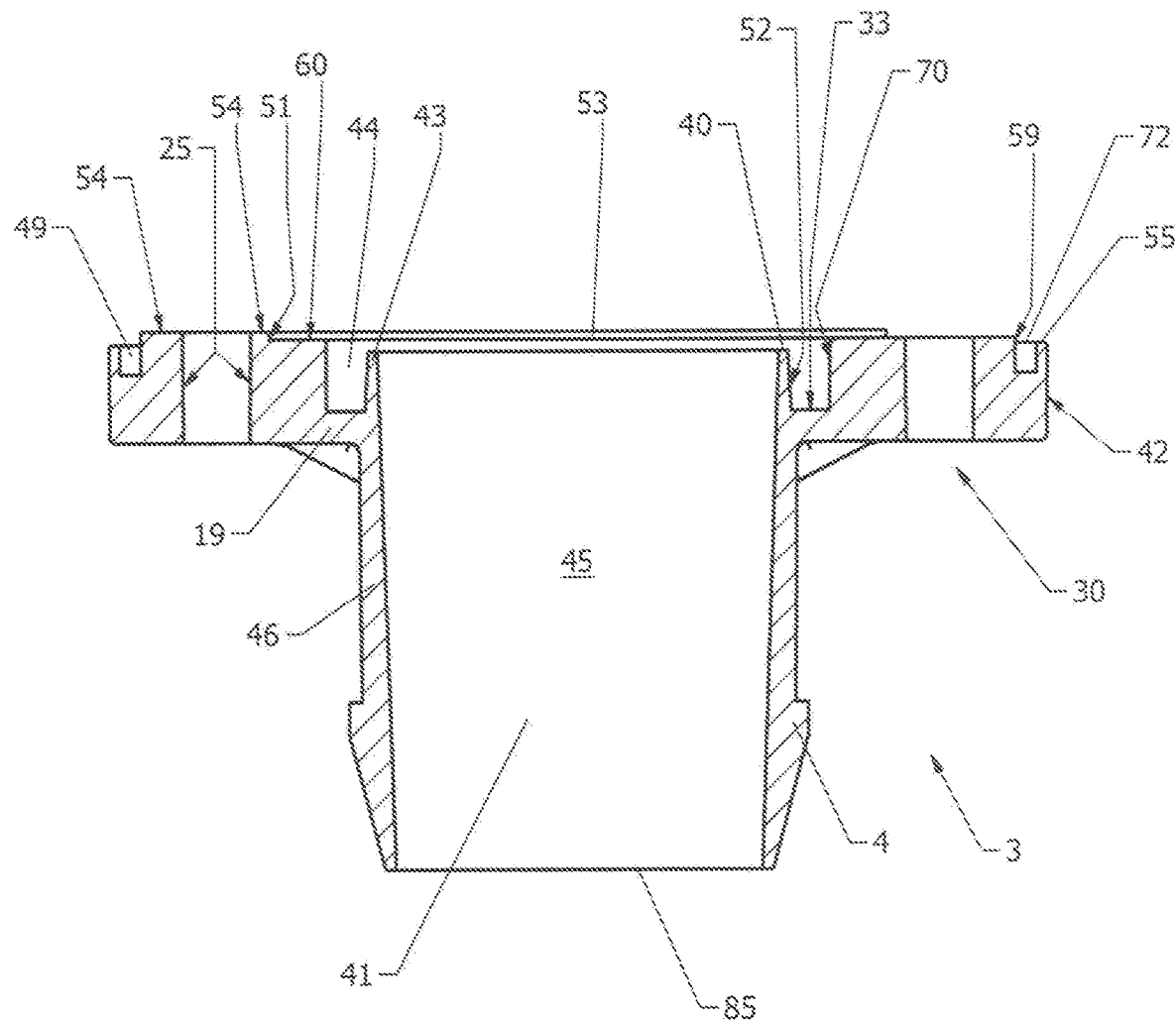
FIG. 3H is a sectional view of the connector component shown in FIG. 3A taken along the direction 3H-3H in FIG. 3A.

In its preferred embodiments, the flange has "fastener holes" 30 (for bolts) and 48 for rivets (FIGS. 3A, 3B, 3G), each of which extends through the flange 14 in a distal-to-proximal direction. The fastener hole surface (for bolts) 25 is shown in FIG. 3A. For example, in FIGS. 3A and 3B, holes 30 and 48 extend from the distal surface 16 of the flange to two such proximal surfaces, the "forward flange surface" 54 and the "recessed flange surface" 60. In FIG. 3G, holes 30 and 48 extend to the distal side of the flange, the distal side being the side visible in that figure. See also FIG. 3C for a side sectional view of rivet fastener hole 48 and FIG. 3H for a side sectional view of bolt fastener hole 30.

The fastener holes are capable of receiving fasteners such as rivets 21 and bolt 10-nut 82 combinations (FIGS. 1A and 1B). The surfaces lengthwise (distal to proximal) inside the fastener holes are referred to herein as "fastener hole surface" 47 (for rivets) and "fastener hole surface" 25 (for bolts).

The recessed flange surface 60 is surrounded on three sides by recessed wall surfaces 51. That configuration creates a recess 53 in the flange. Those walls extend from the recessed flange surface 60 to the forward flange surface 54 where they meet the inner edges 18 of the forward flange surface.

The fourth side 98 of the recess flange surface 60 has no wall so as to be a location where a shield 9 can be more easily slid out of the recess (FIGS. 3A and 3B.) The fourth side 98 is bounded on two sides by recess wall surfaces 51 To further facilitate removal of the shield 9, the rim 55 at the periphery of the flange on the flange proximal side is receded distally in relation to the recessed flange surface 60.

Another major component of the connector is an O-ring 5 (a/k/a O-gasket). Preferably the connector also has a V-ring 7, as described further on.

The connector tube 46 passes through the flange 14 in concentric fashion. The concentric relationship is evident in FIG. 3C as well as in other figures. Also illustrated in that figure are details of how the connector tube and the flange are merged with one another. The merger is effected in a manner that creates a groove 44 (destined to receive an O-ring) between the connector tube and the flange.

A circular collar 19 is interposed between the flange and the connector and is joined to both. (For descriptive purposes, the collar can be considered either an independent item, a part of the connector or a part of the flange.) It can also be seen that the collar is positioned distally in relation to both a flange surface 54 and the proximal end (defined by the connector tube proximal rim 40) of the connector tube. It is, however, closer to the end of the connector tube than to the flange surface 54. The net result is that a groove 44 is created.

The connector tube contributes one surface 52 of the groove (the more central surface) and the flange 14 contributes the other surface, the peripheral surface 70 of the O-gasket groove (a/k/a the inner flange surface). The collar provides, at the distal end of the groove, a third surface 33 (a/k/a O-gasket groove distal surface). That third distal surface 33 prevents an O-ring in the groove 44 from sliding in a proximal-to-distal direction when the flanges of the two joined connectors are forced against each other by pressure.

There is a wall 43 between the groove 44 and the central channel 41. One may select an appropriate thickness for wall 43 such that it is thick enough to provide structural support for the O-gasket groove but otherwise as thin as possible. The thinner the wall, the smaller is the cavity that will be formed in the sealing region between two O-rings 5 when joining two connectors.

In addition to the O-gasket groove 44, the connector comprises a V-gasket groove 49 that is concentric with, but more peripheral than, the O-gasket groove. The V-gasket groove 49 is capable of receiving a V-gasket (a/k/a V-ring) 7 described in detail below. The opening 72 is shown in FIG. 3C. of the V-gasket groove Preferably, but not necessarily, the peripheral surface 66 of the V-gasket groove 49 is recessed relative to the more central wall 59 of that groove to permit expansion of the V-gasket outwardly when facing V-rings of two adjacent connectors are combined.

The terms "tube" and "tubing" have different meanings herein. The term tube is part of the term "connector tube" referred to as connector tube 46. The term tubing refers to tubing 2 (FIG. 1) distinct from the connector, but which can be attached to the connecter tube at the distal end 85 of the connector tube. Tubing can be either rigid or flexible, in the latter case they can be made of plastic, rubber, or other flexible materials.

The connector tube 46 comprises a central channel (a/k/a conduit) 41, which is the lumen of connector tube 46. The connector tube 46 comprises an inner surface 45, which surrounds and defines the central channel 41.

Aspects of the Invention

In a first general aspect, the invention is a connector for facilitating the connection of one piece of tubing to another so that fluid can flow from one to the other in a sterile manner, said connector comprising a connector tube, a flange at one end of that tube, said end being the proximal end of the tube, said flange being at the proximal end of the connector, the other end of the connector tube and connector being their distal end, a circular collar separating said flange from said connector tube so that there is a groove between said tube and said flange, the circular collar provides the distal end of the groove, an O-gasket, said O-gasket inserted into said groove at the proximal end of said connector, said O-gasket encircling the proximal end of the connector tube, a portion of said O-gasket protruding from the flange so as to be capable of contact with the O-gasket of an identical connector when the two connectors are joined at their proximal ends, wherein the flange comprises a recess for storage of at least part of a protective shield, said recess containing at least part of a protective shield, said recess comprising a central opening of diameter greater than the opening at the proximal end of the connector tube, wherein the proximal and distal ends of the connector tube are references for the use of the terms proximal and distal as to all components of the connector.

In some particular embodiments of that first general aspect of the invention, the proximal surface of the flange comprises a forward flange surface and a recessed flange surface, wherein the recessed flange surface is surrounded on three sides by recessed wall surfaces, such that said walls extend from the recessed flange surface to the forward flange surface where they meet the inner edge of the forward flange surface provided that the recessed flange surface comprises as the opening concentric with the connector tube.

In some particular embodiments of the first general aspect of the invention, the flange comprises fastener holes.

In some particular embodiments of the first general aspect of the invention, the fastener holes:
a) are all centered at the same distance from the central axis of the connector tube;
b) are equidistant from each other;
c) as regards the forward and recessed flange surfaces, are either entirely in the forward flange surface or entirely in the recessed flange surface;
d) as regards to adjacent fastener holes, the distance between at least one pair of adjacent fastener holes must be large enough so that their respective fasteners, if in place, will not block removal of the shield;
e) the radial distance from the central axis of the connector tube to the center of the fastener holes is minimized so that the fastener holes are as close as possible to the outer perimeter of the O-gasket groove.

In some particular embodiments of the first general aspect of the invention, two or more fastener holes are fastener holes for rivets and each rivet fastener hole consists of three segments: a narrow segment; a middle segment; and a wide segment; wherein the segments progress from wide to narrow in the distal to proximal direction.

In some particular embodiments of the first general aspect of the invention, two or more fastener holes are fastener holes for bolts designed to accept nuts.

In some particular embodiments of the first general aspect of the invention, the total number of fastener holes per flange is either four, six, or eight.

In some particular embodiments of the first general aspect of the invention, the flange further comprises a groove for a V-gasket, the peripheral surface of said groove at a rim on the proximal side of the flange, said rim at the periphery of the flange, said rim receded distally in relation to the recessed flange surface.

In some particular embodiments of the first general aspect of the invention, the connector is further enhanced with a removable protective shield, said protective shield bonded to a recessed flange surface, the segment of the shield that is bonded being the shield cover segment, said shield cover segment preferably at one end of the shield, said end being the shield cover segment end, the portion of the shield that is not the shield cover segment being the shield fold-back segment, said fold-back segment being foldable.

In some particular embodiments of the first general aspect of the invention, the shield is supplemented with a stiff, perforated partition sufficiently large to cover the shield cover segment, said partition bonded to the fold-back segment of said shield. In some of those particular embodiments, the partition is bonded at a position on the shield such that an edge of the partition is located along a fold in the shield when said shield is folded back on itself to the maximum extent possible absent breakage of any bonds between the shield and the recessed flange surface. In some of those particular embodiments, the partition is between the fold-back segment of the shield and the cover segment of the shield when said fold-back segment is folded back over the cover segment.

A second general aspect of the current invention is a protective cap for attachment to a connector as a described in the first general aspect of the invention and/or its particular embodiments. Said cap comprises a circular cap top attached to a circular cap flange that is disposed around the circumference of said cap top, such that said cap flange will fit around the outer perimeter of a connector flange so as to secure the cap to the connector, wherein said cap top comprises a half pull grip compartment for storage of a half pull grip and one or more rivet compartments for storage of one or more rivets, wherein said cap top further comprises holes that allow movement of air or other gases through the cap top, wherein said compartments are open on the side of the top that faces the connector so as to be capable of holding said half pull grip or rivet when the cap is attached to the connector.

In some particular embodiments of the second general aspect of the invention, the half pull grip compartment comprises an engagement loop compartment, a stem compartment, and a handle compartment, for receiving the half pull grip's loop, stem, and handle, respectively.

In some particular embodiments of the second general aspect of the invention, the cap flange comprises inward protrusions that fit over the periphery of the distal surface of the connector flange so as to secure the cap to the connector flange.

In a third general aspect of the invention, the aforementioned cap (second general aspect plus particular embodiments) is attached to the flange of an aforementioned connector (first general aspect plus particular embodiment) and each of said compartments of the cap is filled with the connector part that it is intended to hold.

In a fourth general aspect, the invention is a connector specified as any of the aforementioned general aspects and/or its particular embodiments, said connector joined to another connector of any one of the above claims, the connectors joined at their proximal ends, either with or without a protective shield present in the connectors.

It is clear that any functional combination of the above aspects and embodiments is part of the current invention.

Construction of the Invention

Detailed descriptions here are for connectors in which the flange comprises 4, 6 and 8 fastener holes, respectively. It is preferred that the flange comprise at least 4 fastener holes. Preferably, the larger the inner diameter (ID) of the tubing, the greater is the number of fastener holes in the flange.

Preferable ranges of use for the connectors are:
- 4 fastener holes: tubing ID from 1.25 inches to 1.74 inches;
- 6 fastener holes: tubing ID from 1.75 inches to 2.49 inches: and
- 8 fastener holes: tubing ID from 2.51 inches to 3.49 inches.

For tubing ID of 3.50 inches or more, the number of fastener holes can be further 2s increased.

For commonly used tubing with IDs of 1.5 inches, 2 inches, or 3 inches, it is preferred that connectors with 4, 6, or 8 fastener holes, respectively, be used.

An example of a connector 3 with 4 fastener holes (a/k/a "4-hole connector") 30, 48 according to the invention is illustrated in FIGS. 1A, 3A-3H. Those figures illustrate a 4-hole connector with two fastener holes 30 for nut 82-bolt 10 combinations and two fastener holes 48 for rivets. A 6-hole connector 101 and an 8-hole connector 103 are showing in FIG. 14 and FIGS. 9A-9B, respectively, as are their respective flanges 102 and 104.

Useful, but flexible, guidelines for placement of the fastener holes are:
1) They are all centered (i.e., the position of their center) at the same distance from the central axis 12 of the connector tube;
2) They are equidistant from each other;
3) As regards the forward and recessed flange surfaces, each fastener hole 30 (for a bolt) or 48 (for a rivet) is either entirely in the forward flange surface 54 or entirely in the recessed flange surface 60;
4) The distance between at least one pair of adjacent fastener holes must be large enough that their respective fasteners, if in place, will not block removal of the two shields 9 from two joined connectors. (Also, to prevent such blockage, the placement of fasteners in holes that open into the recessed flange surface 60 should occur only after removal of the two shields 9 from the recesses (a/k/a recessed compartments) 53 of two joined connectors. See FIGS. 3A, 9B, and 14 for examples of holes that open into a recessed flange 60.
5) Within guidelines (1) through (4), the radial distance from the central axis 12 of the connector tube 46 to the center of the fastener holes is minimized. In general, the centers of the fastener holes should be as close as reasonably possible to the peripheral surface 70 of the O-gasket groove 44. Consistent with guidelines (1) through (4), that should done without interfering with the attachment of shield 9 to the recessed surface 60 and without interference with the function of the shield which is to cover and protect the recessed flange central opening 8 (which is also the flange central opening) and the O-ring 5.

Inside tube 46, fluid may be flowing at high pressure. Therefore guideline (5) is important because when fastening flanged connectors, keeping the fasteners as close as possible to the source of pressure provides the most secure joint. Such fastening minimizes the surface area upon which the pressure may exert its force and therefore reduces buckling of the flange, as compared to when fastening a flange at its periphery. Furthermore, such fastening provides greater anchoring force because fasteners on the flange periphery typically favor anchoring parts on one side of the flange.

It is clear that the criteria for arrangement of the fastener holes are to a large extent independent of the inner diameter of the connector tubes 46 joined by the flange connectors, reflecting the fact that the recommended arrangement of the fastener holes is a "scalable" concept.

Because an intent of the connectors of the present invention is single use and disposability, the preferred connector materials are those that undergo minimal deformation when subjected to pressure; they must also be stable at high temperatures such as those encountered when autoclaving, typically (121° C. and 16 pounds per square inch gauge (PSIG, although those values may be somewhat higher: typically they are less than 130° C. and 20 PSIG) they are stable to gamma irradiation, 50 kiloGrays (kGy), or other forms of sterilization; they are biologically inert; and they are relatively available and inexpensive. Preferred materials for the invention are plastics that are hard at the temperatures used for the connectors; preferred plastics are polysulfones and polycarbonates.

As indicated, the objective of the invention is to form an aseptic connection between two tubings by way of a flange connector attached to one end of each tubing. However when all the fasteners are positioned symmetrically around the flange, the distances between adjacent fasteners are too small to allow the protective shield to be pulled outward past the fasteners, noting that the shield 9 width is about the same size as the width of the recess 53. The objective therefore is to provide the means for extracting the shield 9 past the fasteners, which require positioning within the recessed flange surface 60 and which can obstruct extraction of the shield from between the connectors. The present invention overcomes that problem.

Exploded views of the flange connector are shown in FIGS. 1A, and 1B. A flange connector 3 is connected at its distal end to tubing 2; although that tubing connection may be accomplished by any number of known methods, the illustration shows a tubing connection using a hose barb 4.

FIGS. 3A to 3H show greater detailed of the flange connector 3, according to the invention; specifically, a 4-hole connector is shown and described.

Figure 9A:
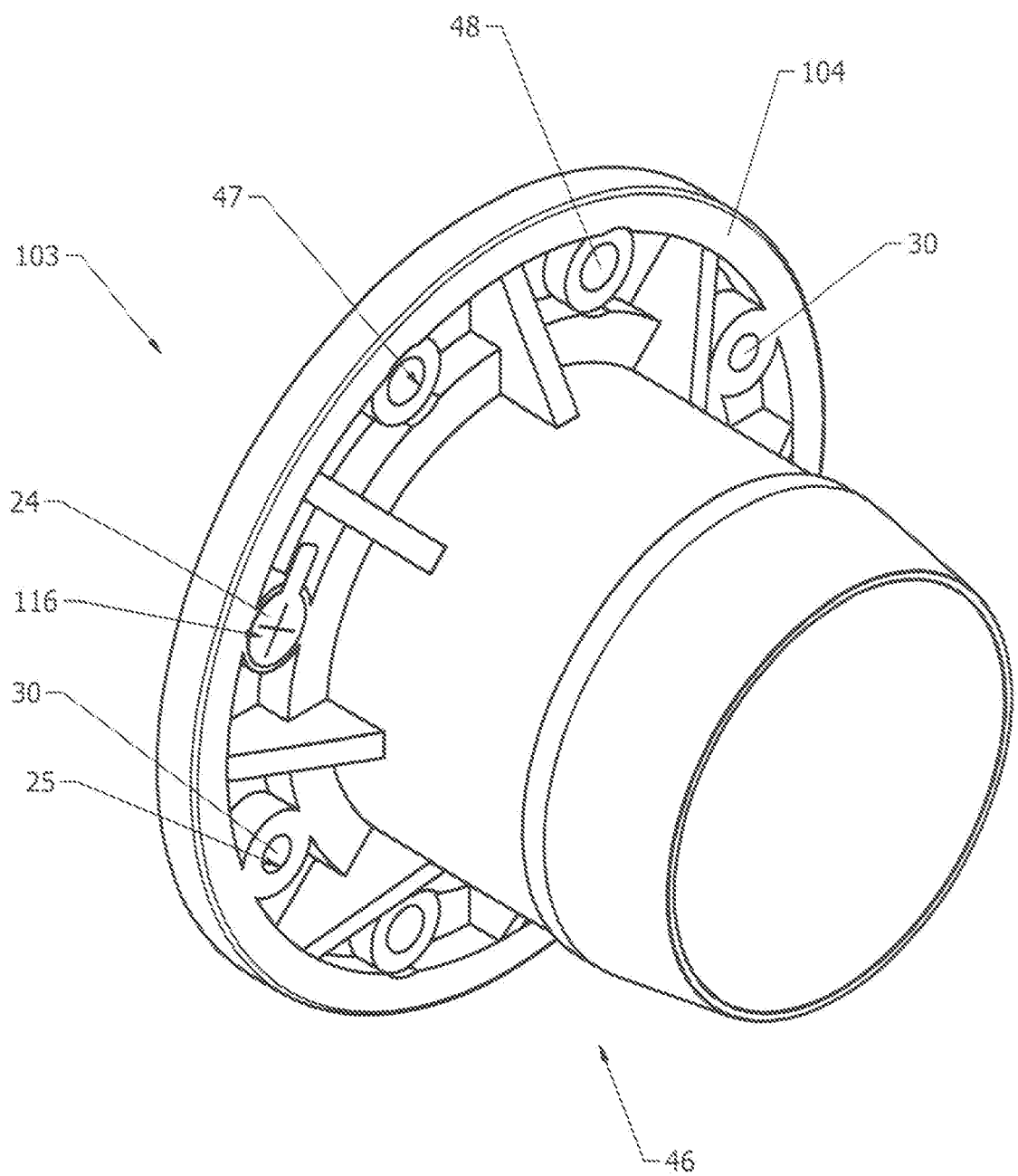
FIG. 9A is a perspective view of the back of an eight-fastener hole connector of the invention.
Figure 9B:
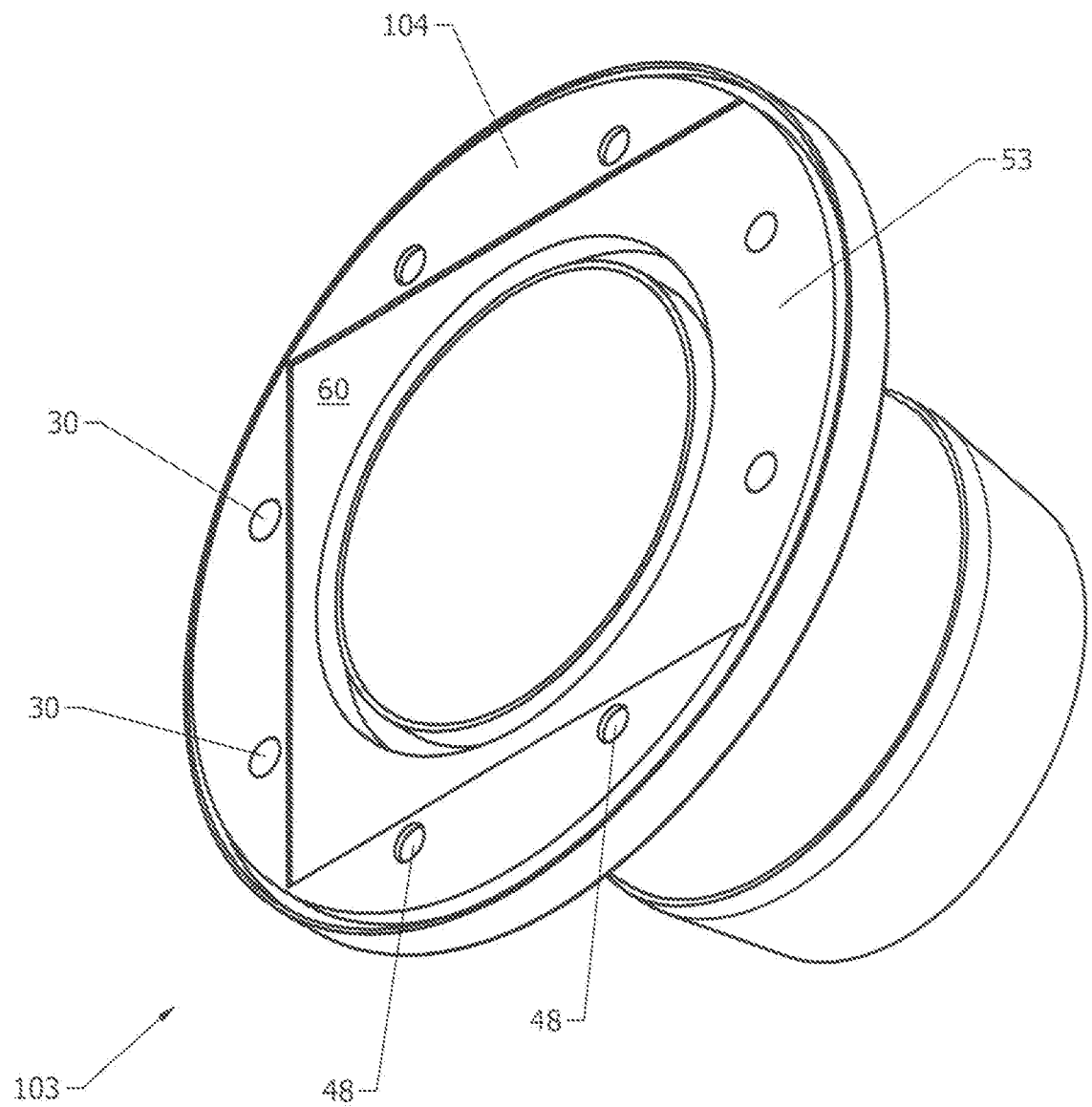
FIG. 9B is a perspective view of the front of an eight-fastener hole connector of the invention.
Figure 10A:
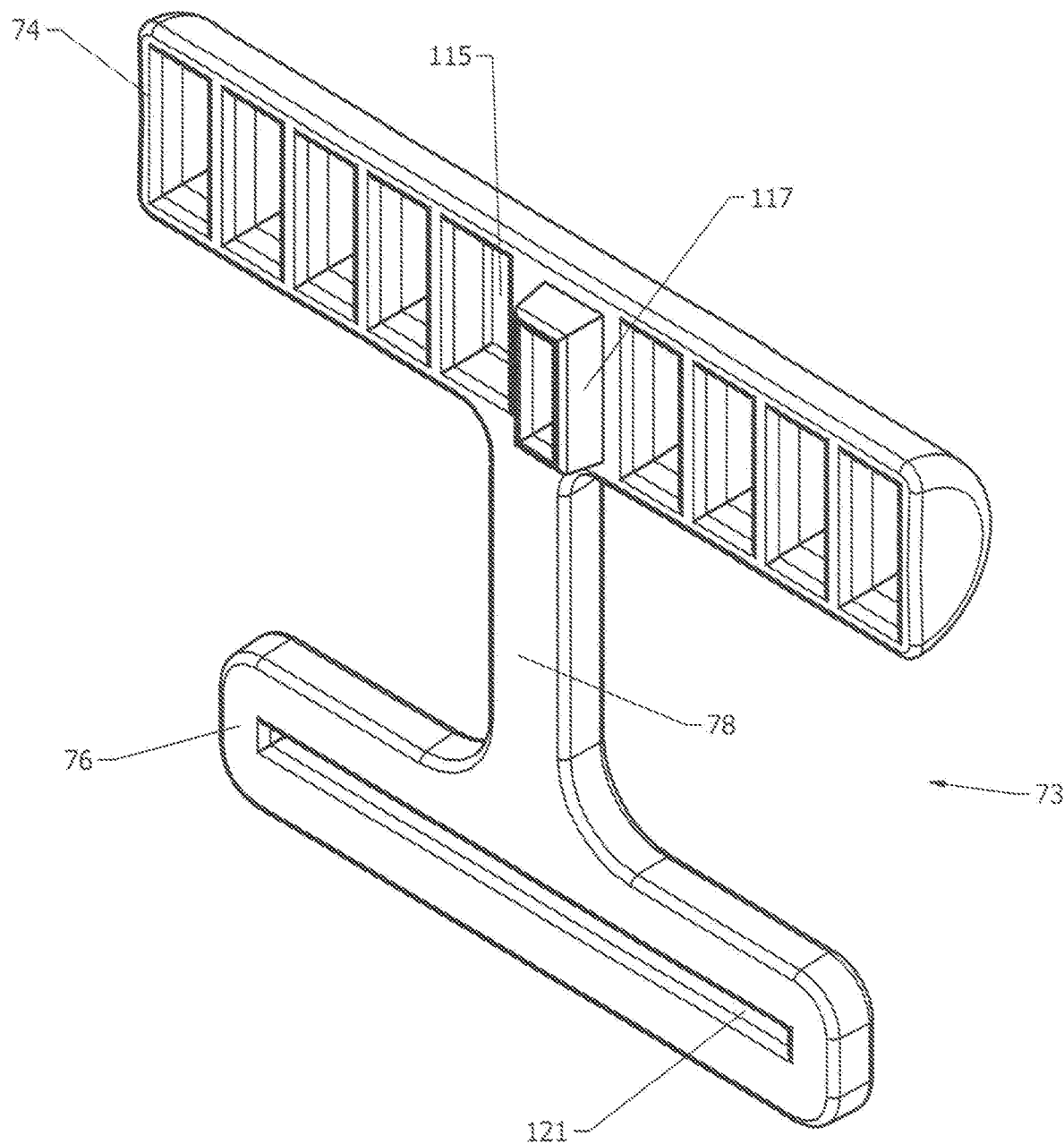
FIG. 10A is a perspective view, part of which is the bottom of a half pull grip.
Figure 10B:
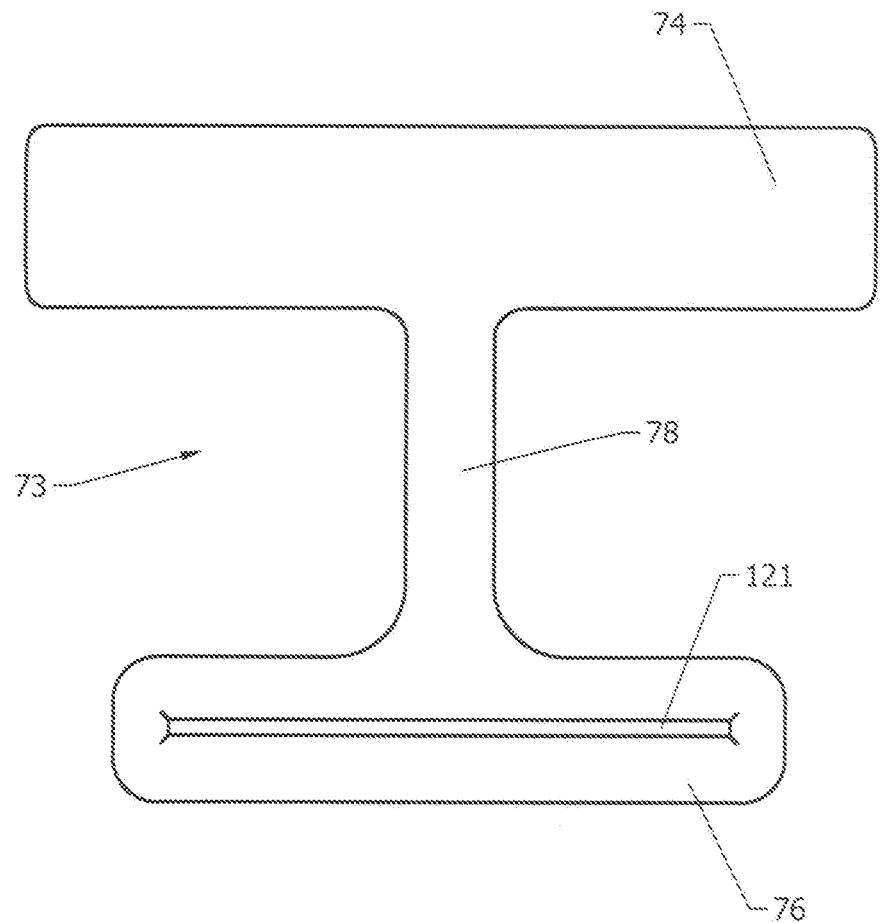
FIG. 10B is a top planar view of the half pull grip shown in FIG. 10A.
Figure 14:
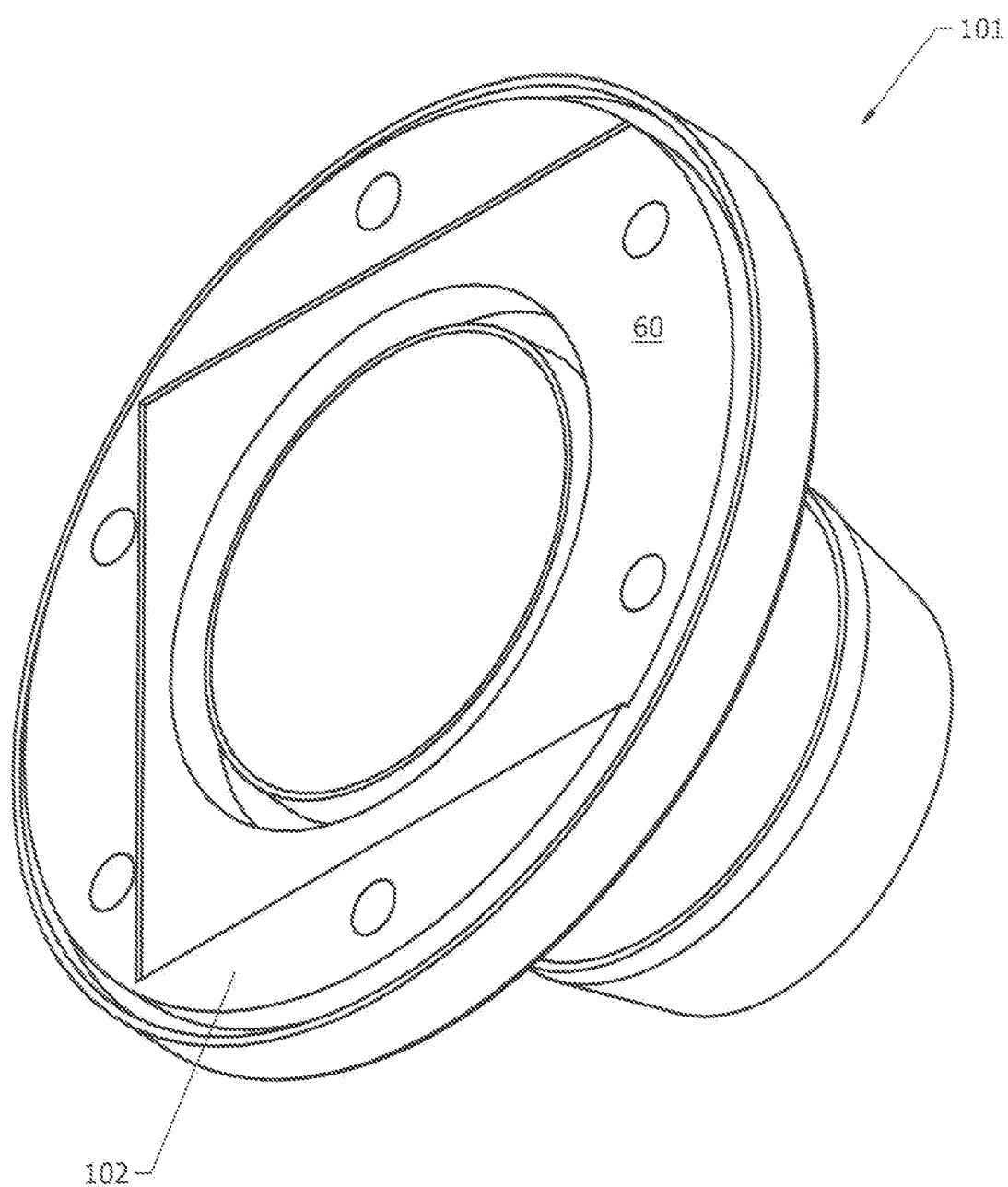
FIG. 14 is a perspective view of the front of a six-fastener hole connector of the invention.

FIGS. 14 and 9B, show 6-hole and 8-hole connectors respectively.

Shield

Figure 4:
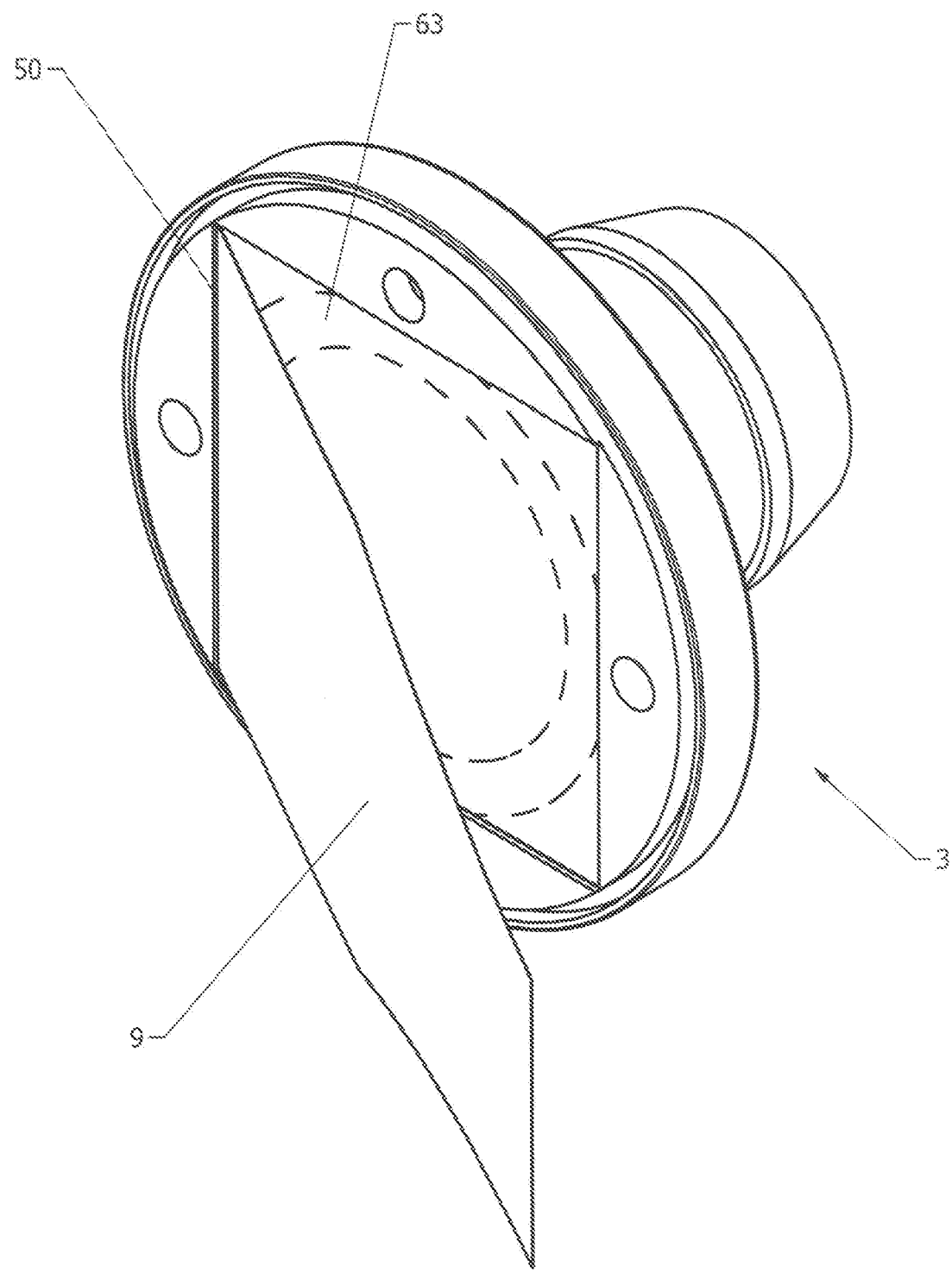
FIG. 4 shows the shield 9 of FIG. 1A positioned in a recess in the connector component 3 of FIG. 1A, with a half pull grip not attached to the shield. The dashed lines define an adhesive bonding area 63 on the side of the shield not viewable in the figure.
Figure 5:
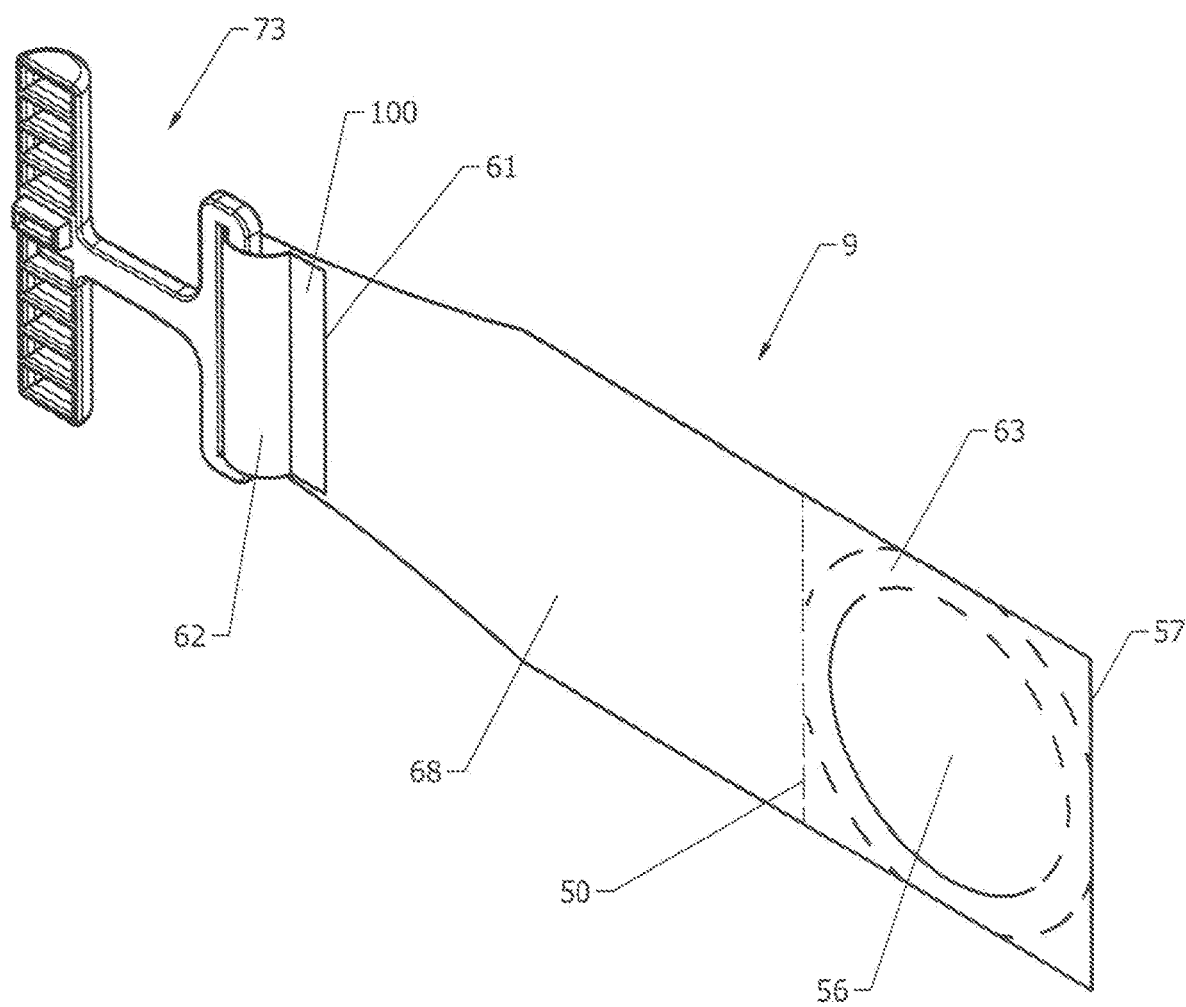
FIG. 5 is a perspective view of the shield of 9 of FIG. 1A with a half pull grip attached. The dashed lines define an adhesive bonding area 63 on the side of the shield not viewable in the figure.
Figure 6A:
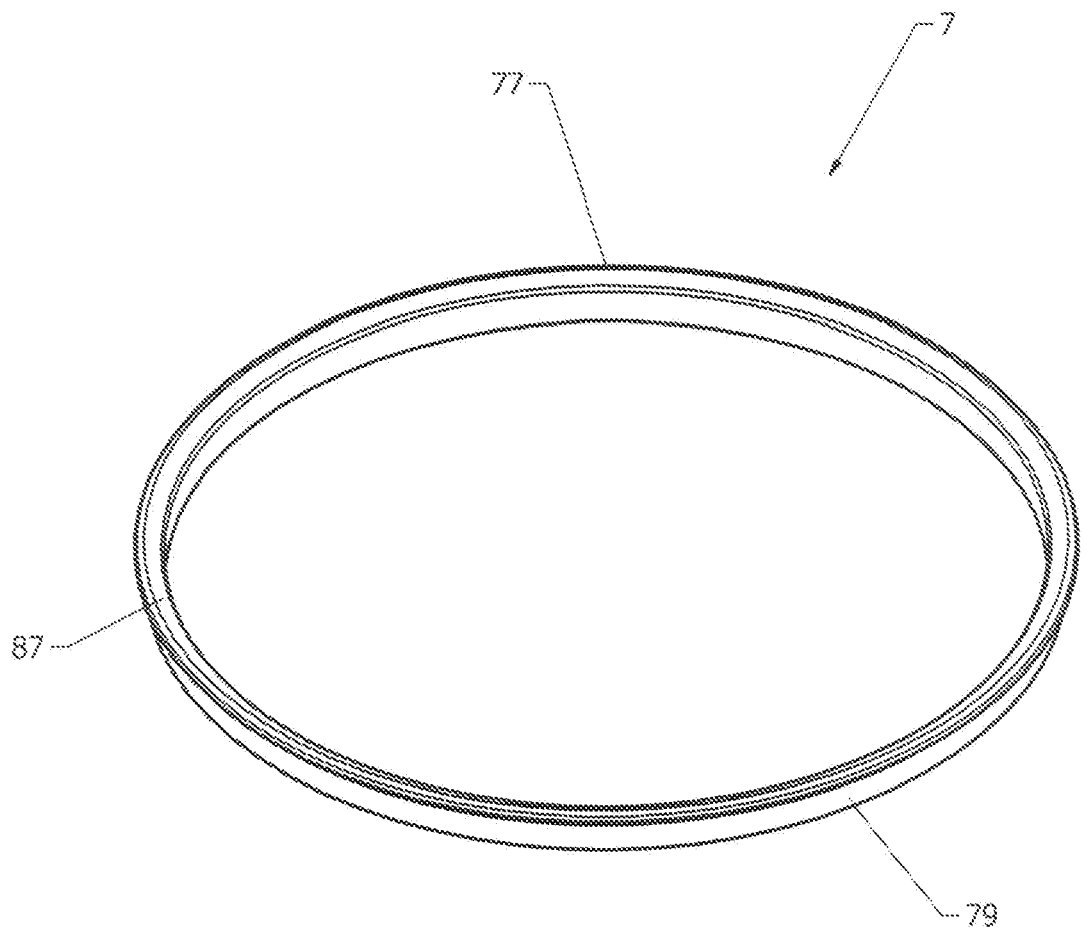
FIG. 6A is a perspective view of V-ring shown in FIG. 1A.
Figure 6B:
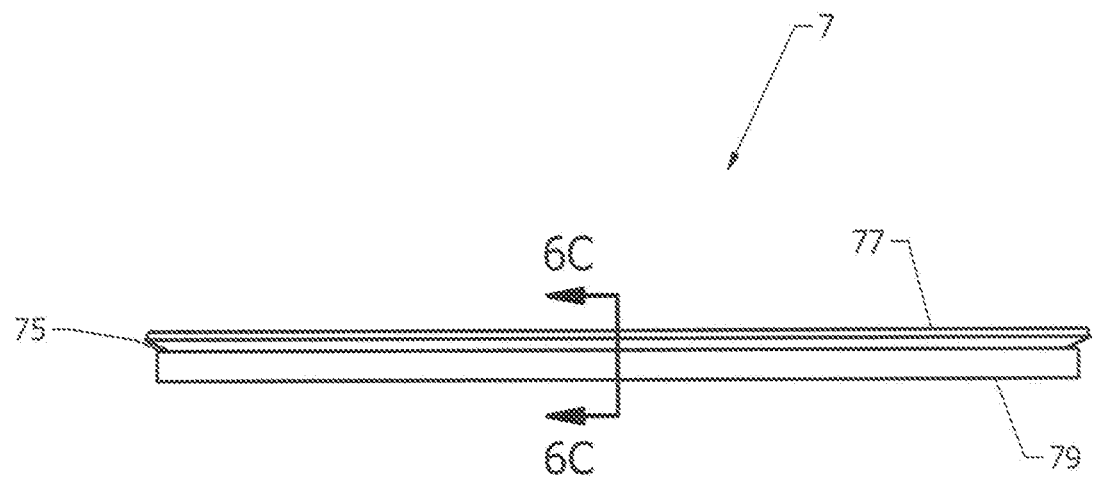
FIG. 6B is a side view of V-ring shown in FIG. 6A.
Figure 6C:
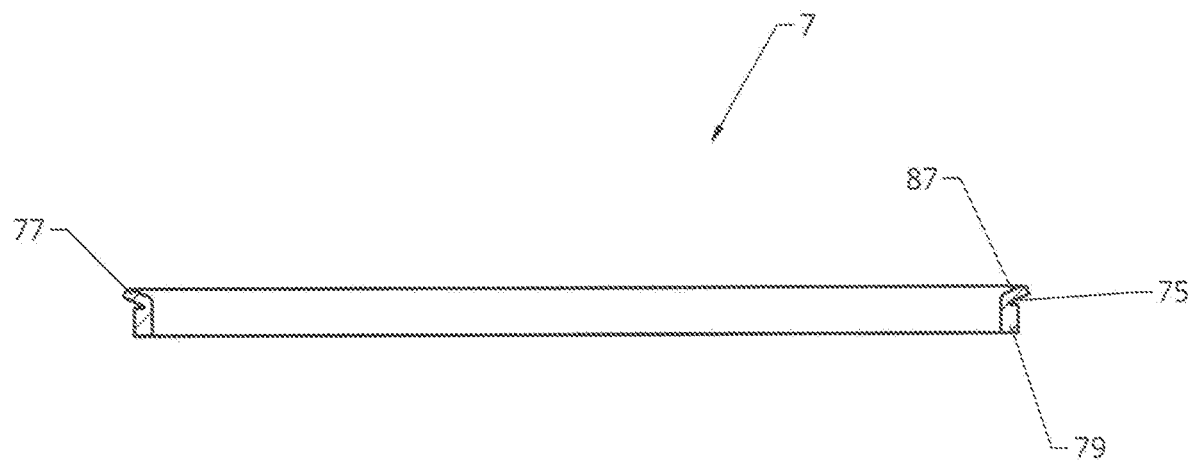
FIG. 6C is a sectional view of V-ring shown in FIG. 6B, taken in the direction line 6C-6C shown in FIG. 6B.

A shield 9 material (FIG. 5), which covers both the proximal opening 6 of the connector tube and the O-ring 5, is attached, glued or welded (in the case of plastics, melted by heat and then cooled) to recessed flange surface 60. The glue or weld is, for example, distributed in between the concentric dashed circles in FIG. 4. Some of the preferred properties of the shield material include permeability to flow of gases across its surface and pores that traverse the shield surface and are sufficiently small so as to prevent contaminants such as microorganisms from passing through the shield. Furthermore, the material should be capable of surviving gamma irradiation, autoclaving and other known sterilization procedures. The shield material should be sufficiently strong so that when one applies a force sufficient to extract the shield from between the connectors, the shield does not tear or deform. A required feature of the material is the ability to attach it to the recessed flange surface 60 and adhesive (e.g., glue) or welding. The attachment, as indicated, may be facilitated by selectively coating a bonding area 63 of the shield 9 and/or recessed flange surface 60 with a bonding agent. Circular bonding areas are illustrated in FIGS. 4 and 5 by the space between the concentric dashed circles, (Use of dashed lines to indicate the area means the area is located on the reverse side of the shield; i.e., the side nonvisible in a figure).

The bonding agent should be able to survive sterilization conditions, heat, or radiation. The bond between the shield material and the recessed flange surface 60 must be sufficiently strong to survive pressure changes during autoclaving; at the same time, the bond must not be so strong as to prevent detachment and removal of the shield during its extraction from between the connectors. The shield bonding area 63 of the shield cover segment 56 (a/k/a shield coupling segment) must be concentric with both the connector tube central channel 41 and the O-gasket groove 44.

A further consideration is the "slipperiness" of both the bonding agent (after the shield-flange surface bonds are broken) and the shield material itself; i.e., after the shield is folded upon itself at fold line 50, it must slide upon itself during its extraction from between the connectors; therefore the shield material must not offer excessive resistance to such sliding. This is particularly true when the two shield surfaces are pressed against each other by the compressed gaskets 5 from joined connectors. Excessive resistance not only complicates extraction of the shield but may also tear or otherwise damage it. Tyvek® is an example of a suitable shield material that meets the above requirements to a great extent.

Tyvek® is the preferred material for the shield 9. To facilitate the bonding of the Tyvek® shield to the recessed flange surface 60, the bonding area 63 on the Tyvek® shield located on its cover segment 56, can be treated with an appropriate adhesive. Such a coated shield, made of Adhesive Tyvek® (zone-coated Tyvek® type 1073B), can be obtained Oliver-Tolas, Feasterville, Pa. Alternatively, a Basic S-3 thermal press from Sonitek, Milford, Conn. can be used to apply heat and pressure to bonding area 63, such that a secure bond is formed between the Tyvek® and recessed flange surface 60. As indicated, the attachment, although strong enough to withstand the anticipated pressure gradients, is not made so strong that the Tyvek® cannot be detached and peeled off by a person using reasonable force and not relying on a machine to effect the pulling.

Other fabrics, screens, membranes, woven or matted, or other forms of synthetic materials may be tailored to achieve the desired results for a particular shielding application. Similarly, one may apply adhesives (such as cyanoacrylates, silicones, polyurethane, epoxies, heat solvents, or other adhesives, or a combination thereof: all of which may be formulated to achieve similar bonding and detachment results.

The shield can be considered to have a series of functionally differing segments (two segments or more can be made of the same material but perform different functions) in sequence from one end 57 of the shield to the other end 61 (FIG. 5): a shield cover segment 56, a shield fold-back segment 68, and a shield loop segment 62. The cover segment 56 covers the gasket 5 and the connector opening 6. The shield overall length is more than twice the length of the cover segment 56. The fold-back segment 68 is of sufficient length that it can be folded back over the entire cover segment 56 and extend beyond the segment 56 and also beyond the flange perimeter 42 while still providing for the shield loop segment 62. In other words, the fold-back shield segment 68 should be long enough so that, after the shield is folded back, the segment is long enough to extend past the flange peripheral surface 42, leaving a shield loop segment 62 outside the flange. The shield loop segment in turn may be looped through half pull grip slot 121 in engagement loop 76 of the half pull grip 73. (In FIG. 7A, the pair 120 of aligned half pull grip slots is shown.) The looped segment is folded onto itself and the overlapping parts are welded together with heat and pressure, such as provided by a typical "bag sealer". An example is AIE 600FL-24 inch Foot Impulse Sealer with 2 mm Seal sold by Uline, Pleasant Prairie, Wis.).

Shield Pull Grip

Figure 7A:
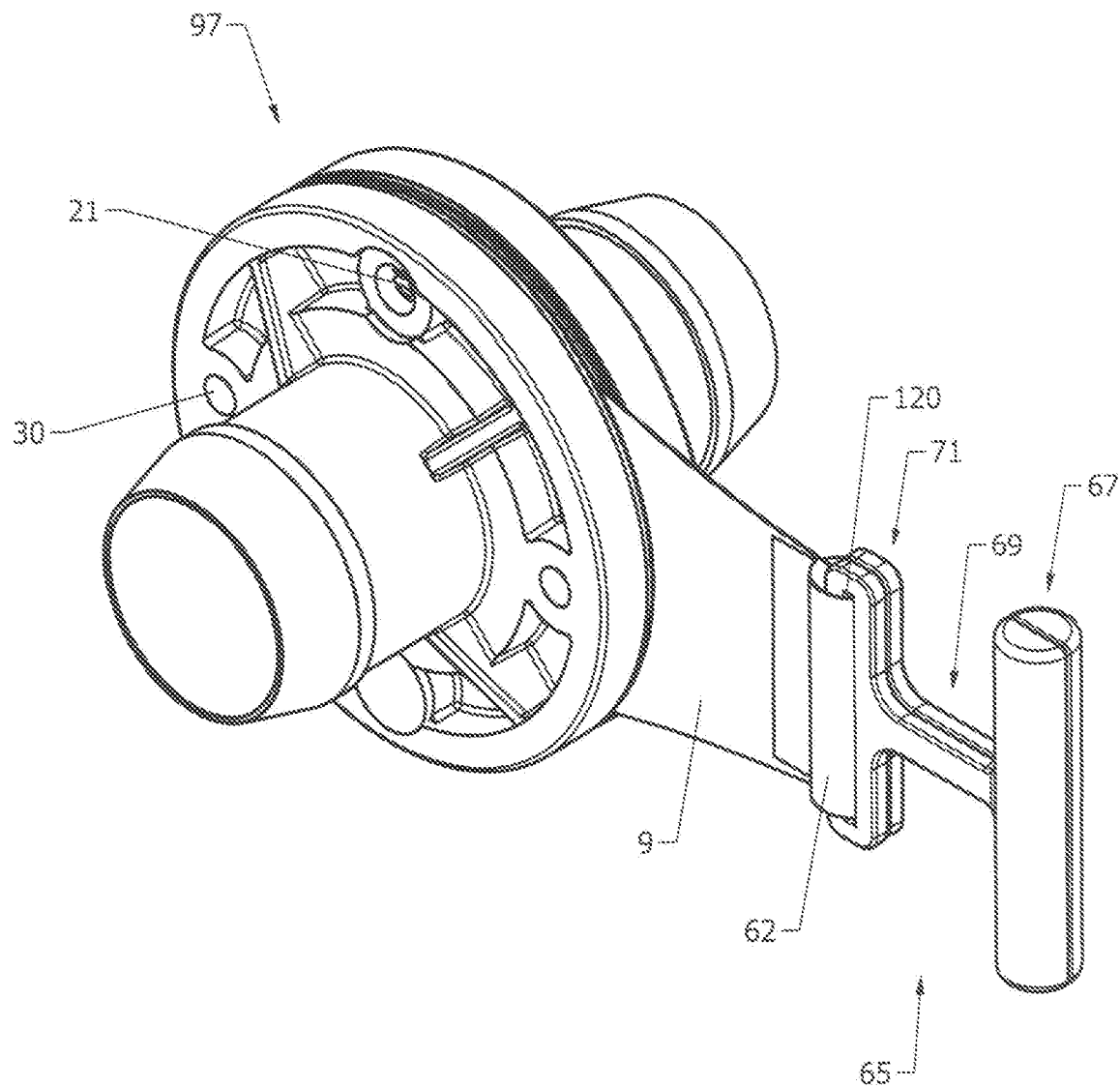
FIG. 7A is a perspective view of a paired four-fastener hole connector of the invention with full pull grip 65 attached to the shields 9.
Figure 13A:
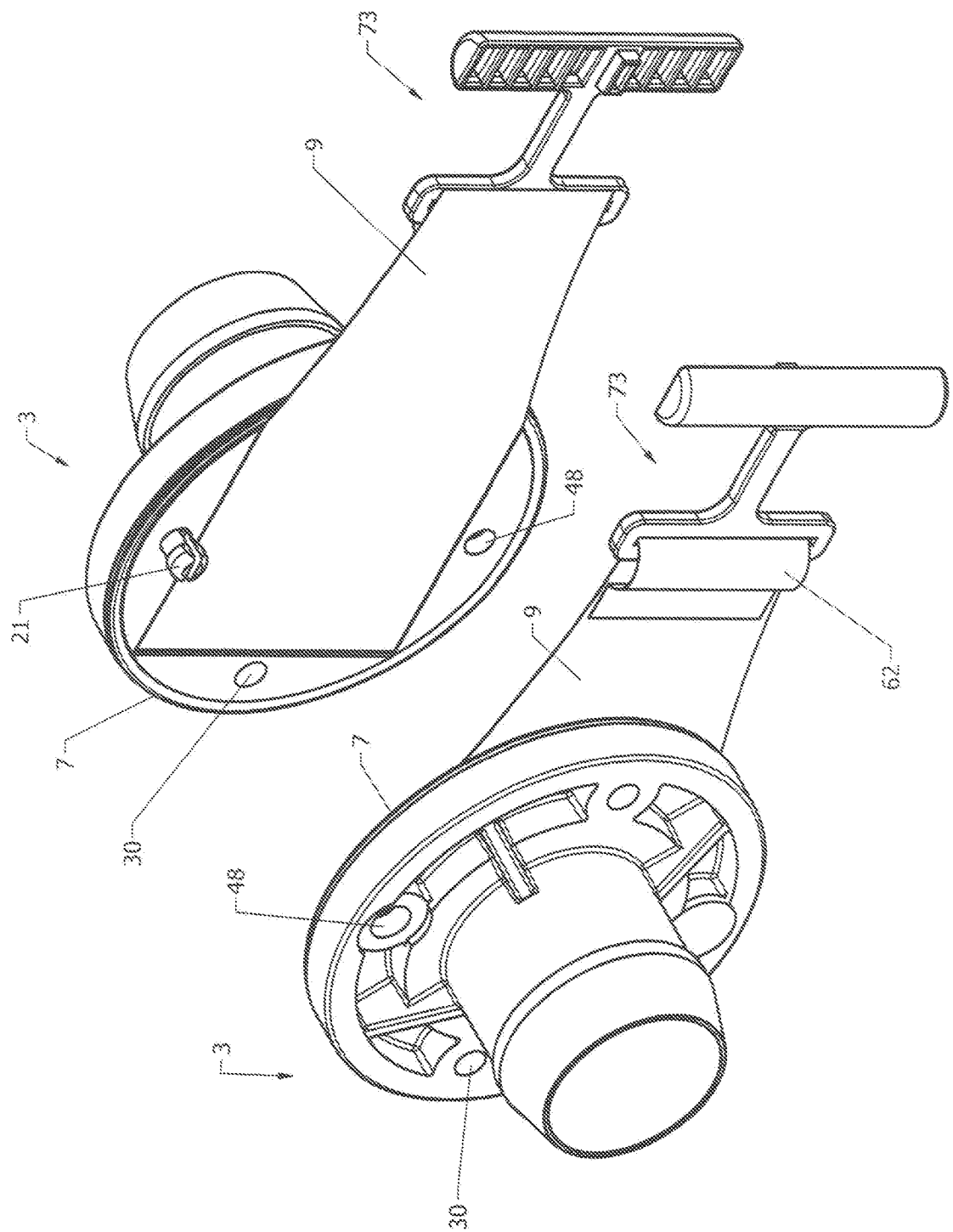
FIG. 13A is an example of a pair of genderless connector components of the invention to be joined with shields adhered inside the recesses of the faces of the connector components and shields attached to half pull grips.

The shield loop segment 62 is long enough to be attached to a half pull grip 73 (FIGS. 5, 7A, 12, 13A and 15). The half pull grip comprises a half pull grip stem 78 with a half-handle 74 at one end and a half pull grip loop 76 at the other end for engaging with the shield loop segment 62. The half handle 74 comprises a member that is solid, straight, and at right angles to the half pull grip stem 78 (Thereby making the shape of the letter T). Two half pull grips 73 can be connected to each other to form a full pull grip 65 comprising a full pull grip stem 69, a full pull grip loop 71 (a/k/a full pull grip engagement loop), and a full pull grip handle 67 (FIG. 7A). An alignment post (a/k/a male segment) 117 in the handle 74 and an alignment post receptacle (a/k/a female segment) 115 in the same handle provide a mechanism for joining and securing the two handle halves. The position of the male and female segments on the handle are such that when the handles are combined the male segment 117 on one half handle aligns with the female segment 115 of the second handle. Similarly segments on the second half handle align with those on the first. The facing half handles are mirror images in that plan. Both half handles are thereby aligned (FIGS. 13A and 7A). The length of the handles 74 is such that an average person may grip the handle with a full hand in order to maximize the force that may be exerted by that person.

Preferably each shield's loop segment 62 is folded into a loop that passes through the loop of the half pull grip 73 Preferably the segment, after it is passed through the half pull grip loop is folded back on itself to be securely attached to the portion of the half loop segment that had not passed through the half pull grip loop. The attachment can be achieved with a strong adhesive, by mechanical coupling or by welding the overlapping segments of the shield's shield loop. To maximize the uniformity of the shield extraction, and to minimize sliding or repositioning of the loop segment within that opening it is preferable that the width of the loop segment 62 and the length of slot 121 in the half pull grip are identical or similar. The net result is that the attached shield 9 is ready to be pulled free of the connector after the protective caps have been removed and the connectors are joined to each other.

Fasteners (Bolts and Rivets)

Figure 7B:
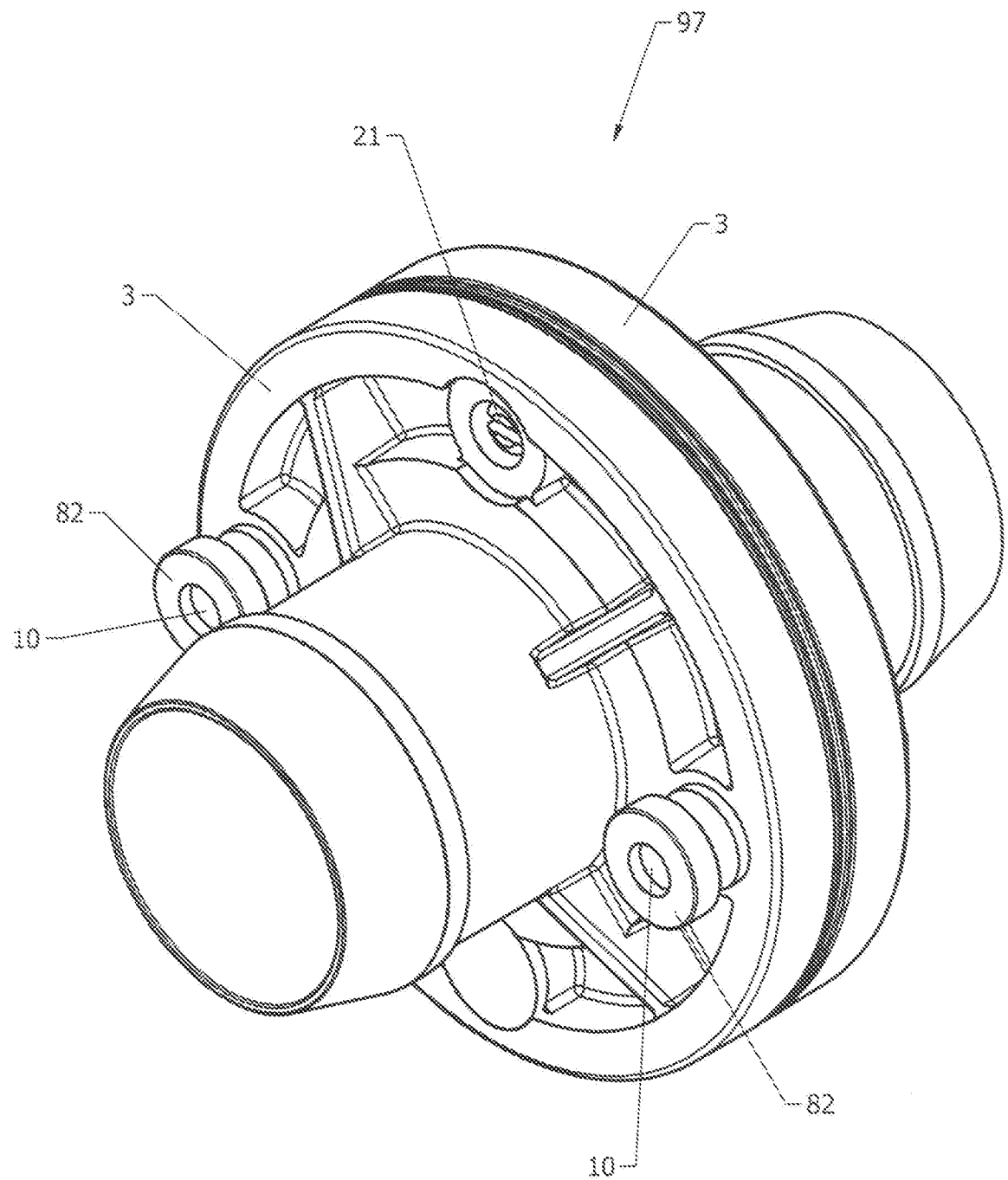
FIG. 7B is a perspective view of the paired connector of FIG. 7A with the shields 9 removed.
Figure 7C:
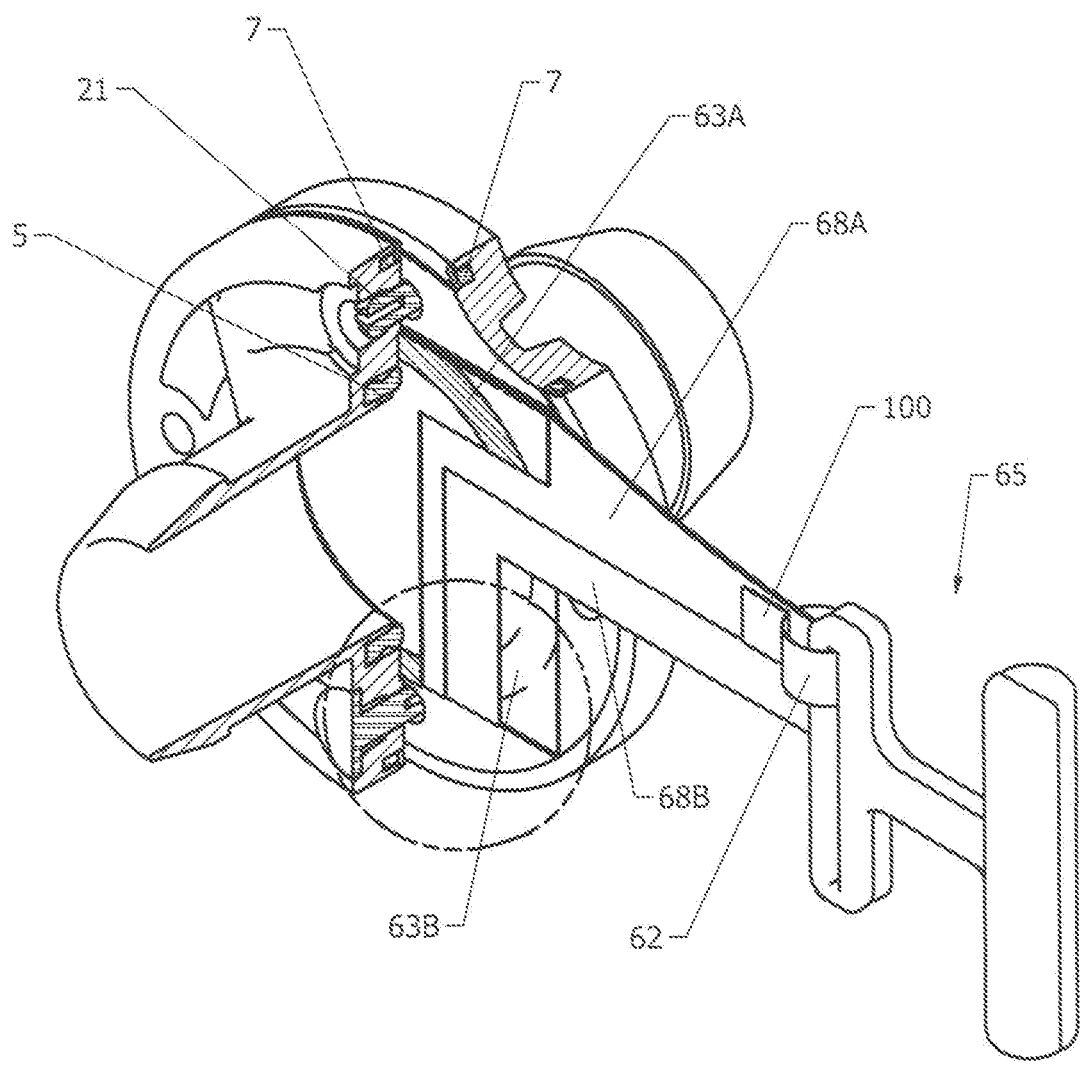
FIG. 7C is a perspective view of a paired four-fastener hole connector of the invention with full pull grip 65 attached to the shields, wherein there are cut-aways to show in detail how the shield layers and gaskets are aligned. The dashed lines define an adhesive bonding area 63 on the side of the shield not viewable in the figure. The crosshatch
Figure 7D:
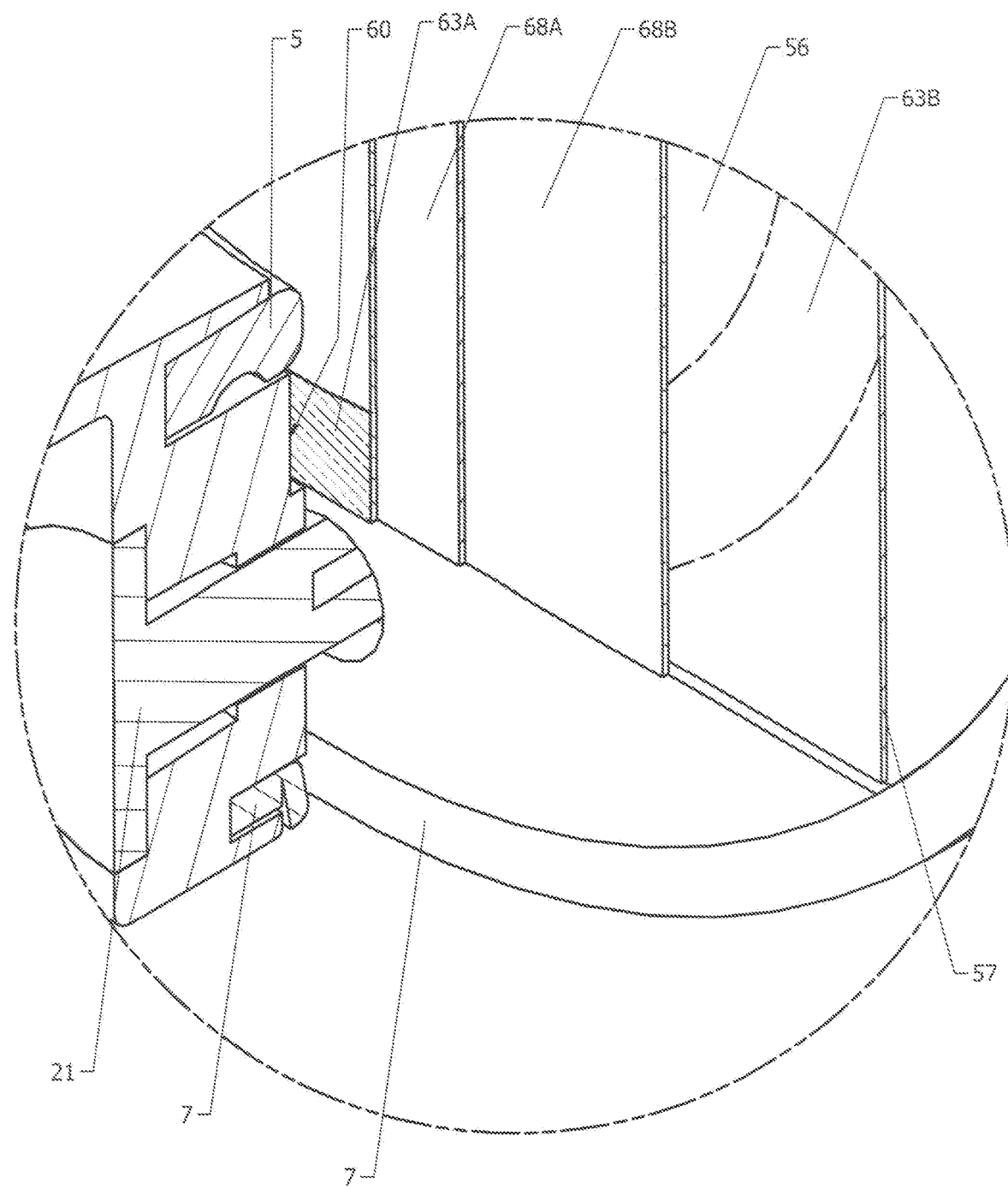
FIG. 7D is an enlarged view of the circled portion of FIG. 7C. The dashed lines define an adhesive bonding area 63B on a shield surface not viewable in the figure. The crosshatched area 63A is an adhesive area on a shield surface viewable in the figure.

The intended use of the invention involves two connectors interfacing so that their respective fastener holes 30 or 48 are aligned and their connector tubes 46 are aligned. As shown in FIG. 7B; the alignment of the two connectors also allows alignment of the fasteners such as a rivet 21 or a bolt 10-nut 82 combination.

The two connectors are forced together until the respective O-gaskets 5 contact each other as much as possible (their two folded protective shields 9 will prevent full contact until they are removed) and their forward flange surfaces 54 are as close as possible to each other (and in fact essentially touch each other once the shields have been removed).

A number of mechanisms may be used to fasten the two connectors to each other, including nuts and bolts, lock and key, and snaps and rivets, as well as others. In the embodiment of the current invention, rivet 21 is a split shank rivet (a/k/a split rivet) (FIGS. 2, 7A, 13A-B).

Because both connectors are identical and contain a single rivet 21 each, the connection may be considered as genderless in nature. However, to create a gendered connector, one places two rivets 21, oriented in the same direction, on the same connector (see FIG. 12). The other connector initially does not have rivets 21. The coupling between these two connectors is achieved, as before, by inserting the rivets from one connector into empty fastener holes 48 in the second connector. The results of the genderless and gendered coupling are identical. (An example of a joined genderless connector pair 97 is shown in FIG. 7A. One method may be preferred over the other depending on the application.

The preferred placement of the rivets on the forward flange surface 54 is that they are on both (long) sides of the shield 9 and are symmetrically placed about the axis of symmetry of the shield (FIG. 13A). The indicated placement of the rivets allows the unobstructed withdrawal of the shields from between the coupled connectors. An example of a preferred binding force on the 4-hole connector (4-fastener holes) using two polysulfone split rivets is about 35 lbs.

One may use more than two rivets. FIG. 9A shows a larger connector, an 8-hole connector, where 4 rivets are used to couple the connectors; two symmetrically placed on each side of the shield. The greater coupling force created by the added rivets assures that the coupling between the two connectors remains secure during extraction of the shields. In addition to the rivets, nut(s) and bolt(s) may be used in fastener holes to further secure the connector.

Shield Confinement and Removal

To remove the paired shields from the joined connectors, one applies a pulling force on the full pull grip 65 in the plane of the recessed flange surface 60 in the direction away from the connectors. It is apparent however that if the surface 60 were uniform and accounted for the entire flange proximal surface, the shield would be trapped between these surfaces when the two connectors are brought together. In that case, for example, the pressure of the "hard" flange surface against the "soft" surface of the shield would greatly complicate extraction of the shield. The presence of the recess 53 or recessed surface 60 alleviates this potential problem.

When folding back the shield fold-back segment 68 relative to the shield cover segment 56, the fold 50—either sharp or curved—will be in the junction between the shield fold-back segment 68 and the cover segment 56. In FIG. 4, a fold line 50 is shown. That fold line abuts the recess wall surface 51.

The depth of recess 53 is the distance between the forward flange surfaces 54 and the recessed surface 60; i.e., the height of wall surface 51. The depth of the recess is uniform over the entire recess. The depth is selected to assure shield clearance such that the shield is not squeezed by forward flange surfaces 54 or recessed flange surface 60 after the connector is mated with another connector. In an example not intended to be limiting, the thickness of the shield is 0.005 inches. With the fold-back segment 68 folded back, the thickness of the folded shield is 0.010 inches. To accommodate that folded shield, the depth of the recess 53 is greater than 0.010 inches; preferably for example, it may be 0.020 to 0.030 inches or deeper. In any case, if the distance of the recessed surface 60 from the forward flange surface 54 is 0.020 inches, the space between the recessed surfaces 60 of two joined connectors will equal or exceed 0.040 inches, more than sufficient to clear the combined thickness of 0.020 inches of the two folded shields. Once the connectors are joined to each other, the force on the shields in a distal-proximal direction along the central axis 12 of the connector tube (and of the connector) will be that exerted only by the elastomeric gaskets 5.

After the shield fold-back segment is folded, a pulling force on that segment will, in significant part, translate into a force that breaks the bonds between the cover segment 56 and the recessed flange surface 60. As expected, by pulling back on the fold-back segment through the pull grip the bonds closest to the fold 50 of the shield will break first. Bond breakage will continue in the pull direction until the entire cover segment 56 is detached and, in fact, removed from between the connectors. Note that as cover segment 56 is removed, it exposes proximal opening 6 in each connector. As the shield is fully removed, connector tube 46 in one connector will fully register with connector tube 46 of the second connector, forming a continuous open conduit.

The amount of force required to remove the shields from between the O-rings is affected largely by factors such as the compressive force exerted on the shields by O-gaskets 5, the surface area of the contact between the shields and the O-rings, and the frictional resistance to sliding of the shields against the O-rings. The fact that a T-handled pull grip can be used will allow a person to remove the shields under conditions whereby all requirements of the invention are satisfied.

The shield withdrawal is guided by the wall surfaces 51 of recess 53, which further assist in the uniform withdrawal.

Paired Connectors

Figure 13B:
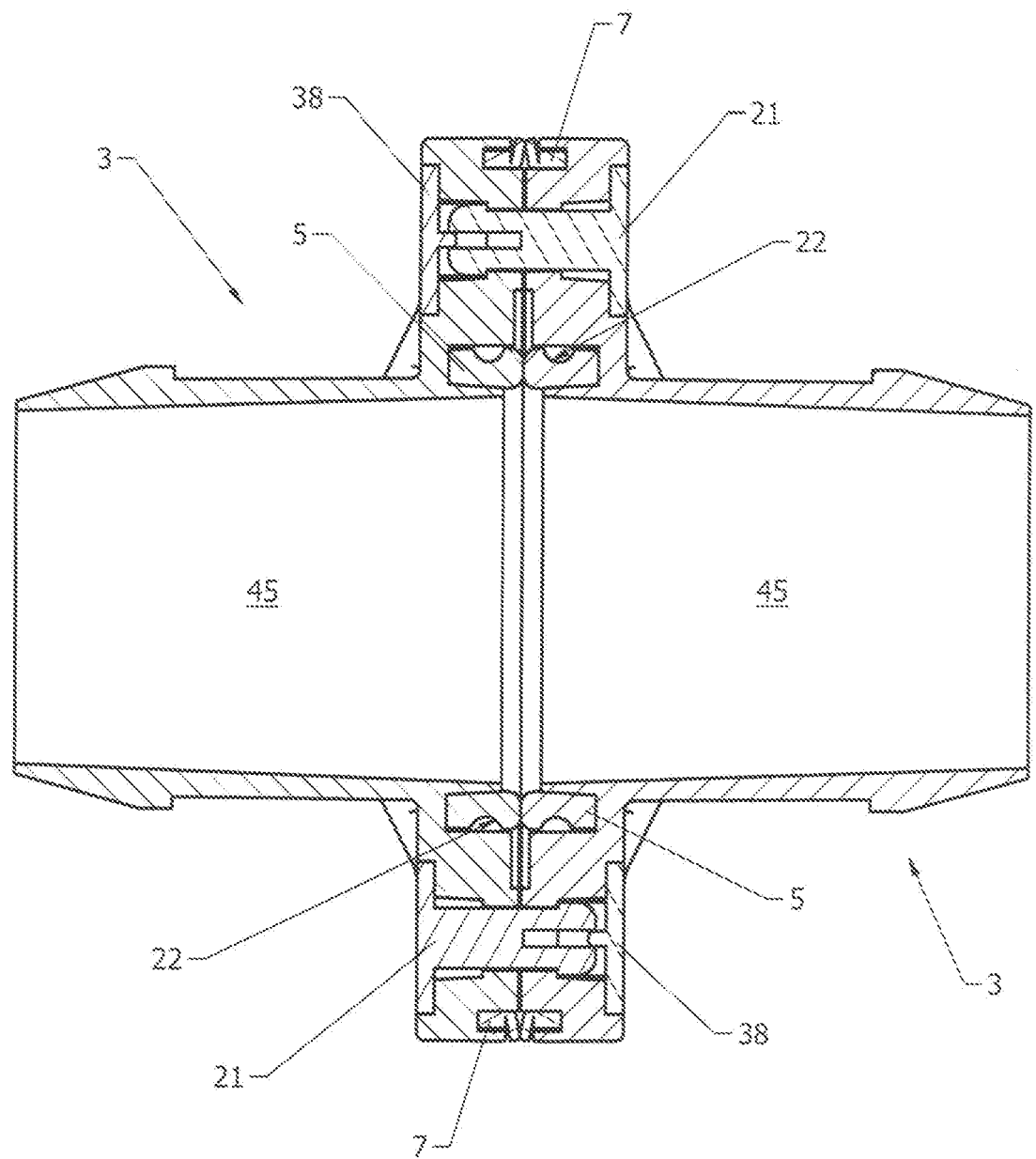
FIG. 13B is a cross-sectional view of the connectors shown in FIG. 13A once they have been joined, the shields 9 removed and rivet head pins 38 added. The view is the same as that shown for an unjoined connector as shown in FIG. 3C.

Two joined connectors with interposed shields are shown in FIGS. 3E, 3F, 7A, 7C and 7D. Two interfacing connectors with their shields removed are shown in FIGS. 78 and 13B. Note that in FIGS. 7C and 70 the shield bonding area 63 of the two shields are denoted by 63A and 63B, respectively. The shield fold-back segments 68 are shown denoted by 68A and 68B, respectively.

O-Ring and Gasket Compression

Central to the sterility goal of the sealing process is the placement of an O-gasket (O-ring) 5 in the O-gasket groove 44 at the proximal end of the connector, encircling the proximal end (defined by the connector tube proximal rim 40) of connector tube 46. The elastomeric nature of the O-rings permits movement of a thin protective shield 9 despite it being sandwiched between portions of each O-ring (FIGS. 3E and 3F) even when most of the O-ring is directly in contact with an O-ring of another connector. That permitted movement, despite the O-ring to O-ring compression, is an essential aspect of maintaining asepsis.

As regards, the O-ring to O-ring compression, consider a previous example, where one layer of the shield is 0.005 inches thick. Two layers from each shield will form a total thickness of 0.01 inches. To accommodate that thickness and still maintain contact between the O-rings after shield removal, each O-ring needs to be compressed 0.01 inches or more. It's preferred that the O-rings remain compressed after the shield is removed to assure a secure barrier at the point where the two connectors merge. In the next example, the connectors are merged with sufficient force to compress each O-ring by 0.020 inches. Accordingly, when the shields are unfurled and completely removed, each O-ring will have expanded slightly but will remain compressed 0.01 inches. That compression will be sufficient to keep the O-rings 5 sealed. Therefore, it's essential to control the level of compression of the O-rings following the merger of two connectors. The mechanism for setting the level of compression is described. That level of compression may be accurately set by controlling the height of the O-ring 5 above the forward flange surface 54 (and also its height above recessed flange surface 60) The calculations of that desired height take into account the height of the O-ring after the shield is removed and the fact that the distance between opposing surfaces 54 is essentially zero or some small number such as <0.010 inches, which is maintained with fasteners, e.g., like the split shank rivet 21. Therefore, once the shields are completely removed; the remaining compression of the O-rings will be set according to the following relationship:

O-ring compression=O-ring height above forward flange surface 54 without compression less half the distance between surfaces 54.

Addition of the remaining fasteners to connect the flanges may be used not only to further secure the flange connectors to each other but also to force the distance between forward flange surfaces 54 to zero.

It follows that an essential aspect of the withdrawal of the shield from between the gaskets is to minimize the distortion of each gasket, maintain the compression of O-gasket, and retain each gasket in position during shield withdrawal. The O-gasket groove peripheral surface 70 and the O-gasket more central surface 52 provide the barriers that retain the gasket in the desired position despite forces attempting to pull it perpendicularly to the central axis of the connector during withdrawal of the shield. One preferred shape of the gasket is one that is longer along its proximal-distal axis (that axis being parallel to the central axis 12 of the connector tube) than its wall thickness.

A preferred shape of the gasket is shown in FIG. 13B. Here there is a cut-out portion 22 in the O-ring, allowing more of it to remain in the O-ring groove 44 when under compression. The cut-out is in a gasket whose cross-sectional shape at one end is consistent with that of a rectangle and at the other end is consistent with that of an oval. However, many cross-sectional shapes are possible.

Most of the gasket is inserted into the O-gasket groove 44 in elongated fashion. This provides an increased anchoring of the gasket in the gasket groove. In addition to the increased anchoring effect of the elongated O-gasket 5, the height of that gasket permits the gasket to extend from its groove to beyond recessed flange surface 60 and, when the shield 9 has been removed, beyond the forward flange surface 54.

Compression of the O-gaskets along their long (proximal to distal) axes results in their expansion perpendicular to that axis, both radially outward from that axis and radially inward toward the central axis 12 of the connector. When a gasket 5 expands under compression, it is forced against O-gasket groove walls 52, 70 which further secures the gasket 5 in its groove 44. With increased compression of the O-gasket, the gasket may also expand into space outside the gasket groove.

The radial expansion of the gasket is possible because of the gap between the corresponding O-gasket grooves 44; when the flange connectors are joined, the corresponding proximal edges of peripheral surfaces 70 of the O-gasket grooves 44 are separated from each other by the combined depths of the recessed surfaces 60 relative to their respective forward flange surfaces 54 This separation is more pronounced for the more central wall surfaces 52 of the O-gasket groove, which are recessed relative to recessed surface 60 so that when those forward flange surfaces 54 touch each other, there is added space for expansion of the gasket in the inwardly radial direction. The existence of that space will accommodate a slight "rolling" of the gaskets during withdrawal of the shield, which in turn facilitates the initial movement of the shield and the severing of the bond between the shield and the recessed flange surface 60. That gap is kept short enough, however, to assure that compression between the gaskets is retained during withdrawal of the shields or during "full" vacuum (as may encountered during steam sterilization, about 26" Hg).

O-rings of any suitable rubber, plastic, or other compressible material may be used Examples are silicone EPDM, Viton, and the like. They must, however, meet the specification of the connector, e.g., biological safety (Class VI material) so that they can, for example, be irradiated with gamma radiation, autoclaved, or chemically sterilized and have the elasticity required, 40-70 durometer hardness.

Rivets/Fasteners

Figure 2:
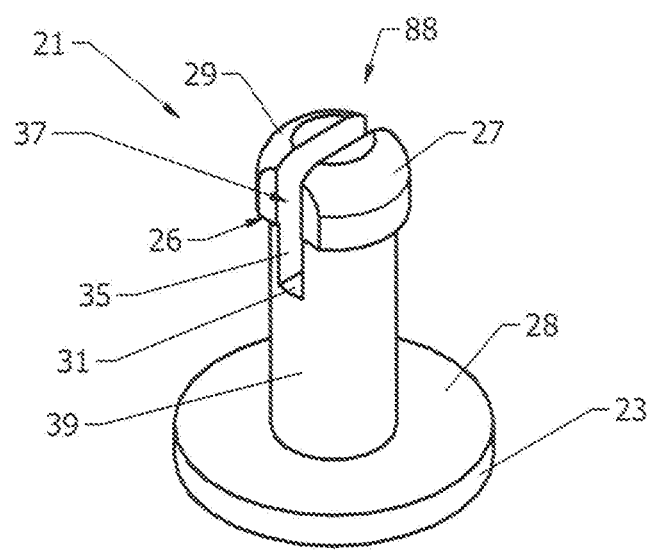
FIG. 2 is a perspective view of the rivet 21 of FIG. 1A.

The rivets 21, FIG. 2, provide a simple mechanism to align the opposing connectors 3, lock them together and set the distance between them. FIGS. 3E and 13B show the placement of the rivet within its designated rivet fastener hole 48. Note that the rivet cap 23 is received by the countersink 91 (a/k/a wide segment of the rivet fastener hole 48), which fixes the position of the rivet. The base 28 of the rivet cap sits flush with the surface that is the wide countersink flat 93. Glue, mechanical fastening or some other means may be used to secure that position. The stem 39 of the rivet and its head 27 extend through the rivet fastener hole 48 to emerge from the forward flange surface 54 of the connector. The length of the rivet stem 39 (from the base 28 of the cap 23 to the base 26 of the head 27) is equal to or marginally longer than the combined depths of the middle segment 95 of the rivet hole 48 and the narrow segment 92 of the rivet hole 48 (FIGS. 3D and 3E). (The third segment of the hole is the wide segment 91.) That is the distance the rivet stem 39 has to span when it is connecting two flange connectors that are touching each other or are in close proximity to each other. (The surface 96 of the middle segment 95 is also shown in FIG. 3D).

Rivet head 27 is preferably a split shank rivet head and has a diameter that is greater than the smallest diameter of rivet fastener hole 48, i.e., greater than the diameter of narrow segment 92. The rivet head is capable of collapsing to the extent of the width of the split 37 in the rivet head (a/k/a gap 37 in the rivet head). The split in the rivet head is defined by a surface of a wall 35 on either side of the split and the bottom 31 of the split in the rivet head. Insertion of rivet 21 into the fastener hole 48 of the opposing connector forces the two halves 29 of head 27 to collapse toward each other, reducing the overall diameter of the head, thereby enabling its insertion into rivet fastener hole 48 narrow segment 92. Pressing the two connectors together allows the rivet to be fully inserted into segment 92 of the fastener hole 48. Once the rivet head clears segment 92 and the surface that is the narrow countersink flat 94 of the opposing connector, the two halves 29 of the split head are free to expand to their original position. The head 27 is now wider than the diameter of narrow segment 92 of hole 48. The rivet head base 26 expands over the narrow countersink flat 94 and therefore cannot be withdrawn. As a result, the two connectors are locked in position.

Figure 8A:
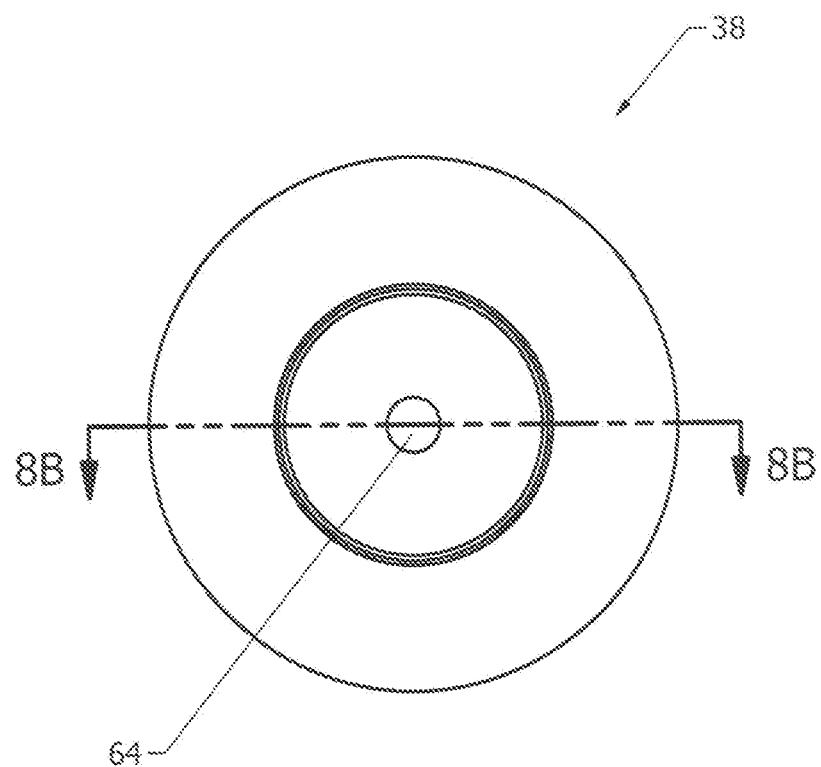
FIG. 8A is an example of a bottom planar view of a rivet head pin of the invention for maintaining a rivet attached to a pair of connectors.
Figure 8B:
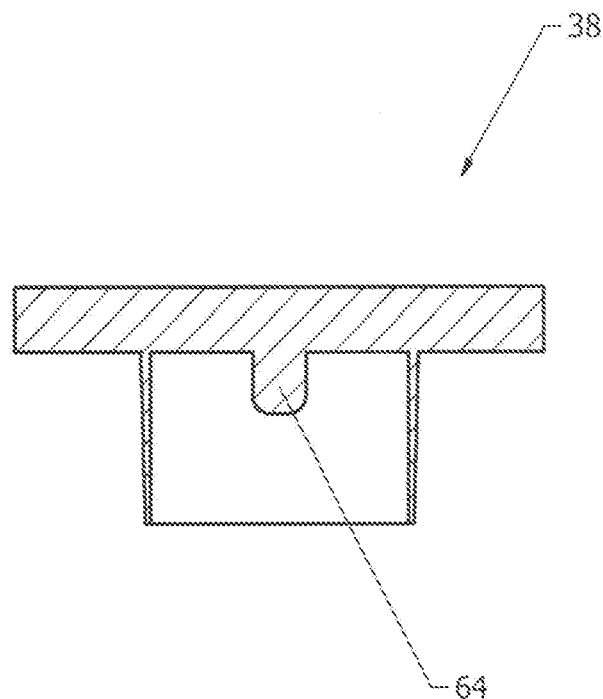
FIG. 8B is a sectional view of the rivet head pin shown in FIG. 8A taken along the direction 8B-8B in FIG. 8A.

Although the rivet creates a tight link between the two connectors, one may reinforce such a connection by using any one of a number of known mechanisms. Selection of rivet material that is stronger is one example. Another example involves insertion of a pin stem 64 (Show in FIGS. 8 and 13G) or similar device into the gap 37 between the rivet head halves 29. This insertion will prevent the halves of the rivet head 27 from collapsing inward, and keep the rivet head locked in position even under increased force. Insertion of such a pin may be accomplished manually with a rivet head pin 38 such as shown in FIG. 8. Alternatively, but not necessarily, it may be accomplished automatically for example by placing the pin under spring tension while the pin end is positioned axially and centrally in relation to the fastener hole 48. The length of the pin, when fully extended, is sufficient to extend the pin below the apex 88 of the rivet head and into the split 37. When the rivet 21 is making its passage in hole 48, the halves 29 of the rivet head are together and gap 37 between them is essentially closed. As the rivet head is pushed forward it pushes against the pin, forcing the pin back against the spring. As the base 26 of the rivet head clears the narrow countersink flat 94 of the opposing connector rivet fastener hole 48, the head halves 29 snap back to their original position, gap 37 opens, allowing the pin to extend by spring action into the gap. A pin having nearly the same diameter or width as the gap 37 will prevent the convergence of head halves 29, locking the rivet in position.

A platform formed by the apex 88 of the half rivet heads 29 (or a conical or wedged countersink at the apex 88) may be used to guide the pin or wedge. Alternatively, someone skilled in the art may use different rivets, of different configuration or material to achieve similar results; furthermore, one need not use rivets that snap to lock. One may use other locking mechanisms such as twist or turn mechanisms or use a wedge to fix a position or use a screw or nut and bolt, as well as other mechanisms, or any combination thereof.

V-Ring

It is possible that the described flange connectors may be used in less than sanitary conditions. As a result, it is preferable that the connector of the present invention incorporate a second gasket, a V-gasket 7, at the periphery of the flange on the proximal side of the flange. As shown in FIGS. 3D, 3E, 3F, 6A-C, and 13B, a gasket 7 with a V configuration is anchored to the periphery of the flange of the connector. The gasket contains an anchor segment 79 that insets into the V-gasket groove 49, defined by its more central surface 59 and its peripheral surface 66 and which has an opening 72. The arm 77 of the "V" extends outward from the connector flange at about a 45 degree angle (FIGS. 6B and 6C) When two flange connectors 3 are combined, not only do the internal O-gasket 5 compress against each other, but the facing V arms 77 are also pressed against each other, thereby sealing the perimeter between the connectors (FIGS. 13B and 3E). The pressed V arms 77 do not compress in exactly the same manner as the gaskets 5; rather, the proximal surfaces 87 of the V-gasket arms are pressed against each other to form a seal. The V-gasket slot 75 at the base of the arm 77 allows the arm to swivel away from the pressure while maintaining the seal. The pressure of the V-gaskets against each other comes not from compression but from the springiness of the material and its natural tendency to return to its original shape. Such a seal does not present a significant force against the shield when it is pulled out. The V-gaskets not only provide a barrier to air-borne particles, but also a barrier against possible liquid spills.

Fastener Opening Covers

The connectors of all sizes are preferably supplemented with thin protective covers 24 to cover the openings to the fastener holes (FIG. 9A.) The covers may be removable prior to insertion of the fasteners, or the fasteners may be simply inserted through their respective holes by breaking through the covers, which may be scored covers to aid in the insertion and alignment of the fastener. A typical thickness may be 0.001 inches to several thousands of an inch. Such thin covers may offer full protection against contamination and minimum resistance to insertion and positioning of the fasteners. The covers may comprise a narrow slit(s) to make it easier to insert fasteners through them without allowing excessive air to pass through them prior to fastener insertion. A cross-shaped slit 116 is shown in FIG. 9A.

Shield Partition

Figure 15:
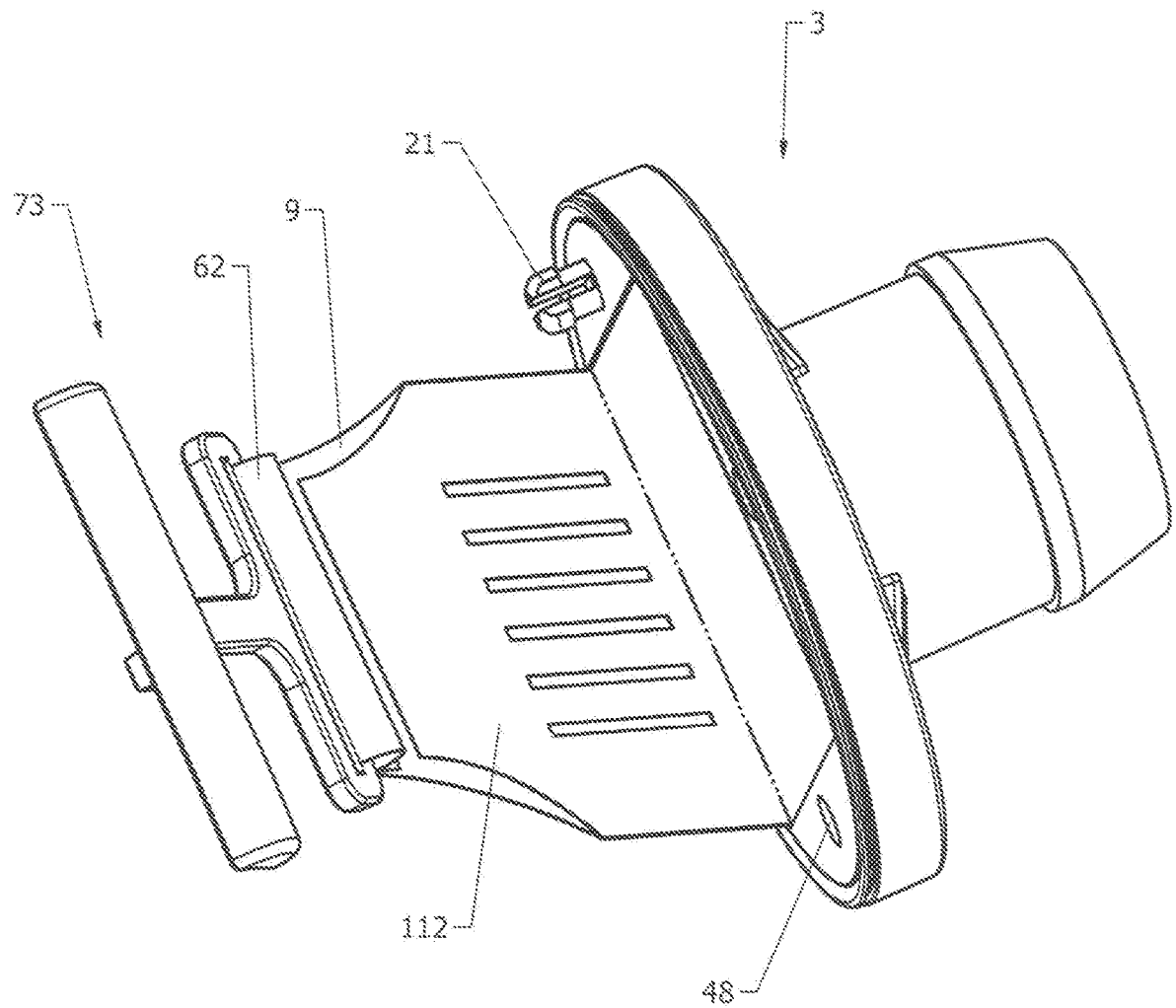
FIG. 15 is a perspective view of a genderless connector of the invention with half pull grip 73 attached to shield 9 and a shield partition 122 added.

It is also envisioned that the shield 9 may be supplemented with another partition or layer 112, the function of which may be multifold (see FIG. 15). The following are some examples: A partition (a/k/a shield partition) 112 between the cover segment 56 and the fold-back segment 68 of the shield, which consists of a thin, stiff material, may be used to protect the cover segment 56 of the shield; i.e., during autoclaving when extreme transitions in temperature (about 125° C.) and pressures (up to about 20 psig) are common, the partition may serve to keep the cover segment 56 flat and prevent its expansion. Perforations in the partition permit gas flow through the partition for pressure equilibration. The preferred shape of the partition over the cover segment 56 is at least the same as that of the cover segment 56 but may extend and attach to other shield segments. The thickness of the partition is preferably minimized while maintaining the stiffness of the material. A thickness of about 0.001 to 0.010 inches of material such as polyimide or kepton may serve that purpose. It should be noted that addition of such a partition will add to the thickness of the shield overall, which will require an increase in the gasket 5 compression in order to meet the compression goals discussed above. The partition may serve to keep the shield material from folding or shifting and on track between recess wall surfaces 51 during its extraction from between the connectors. A partition with a low coefficient of friction may facilitate the extraction of the shield. Preferably the partition end is bonded to the shield at a point most distal from the point of initial detachment of the shield from the recessed flange surface 60. Such a partition is envisioned to be more beneficial with a large flange connector that has a large bore inner diameter.

Connector End Cap

The connector protective cap 11 (FIGS. 11A and 11B.) is a covering for the flange 14 and its components. However, in addition to providing a covering, it serves additional functions including, for example, enclosing and protecting rivet(s) 21. It also encloses, organizes and protects the entire shield 9, including the half pull grip 73 to which the shield is attached. It also confines and protects the fastener holes 30 and 48, particularly on the proximal side of the flange. Compartments in the face of the cap (the side of the cap that interfaces with the proximal end of the connector) confine the rivet(s) 21. Another compartment 143 in the face of the cap receives the half pull grip so that it is "flush" with the inner surface of the cap. The cap provides sufficient space to receive the arm of the V-gasket 7. Another important function of the cap is to provide a backing to the face of the flange. The relatively flat nature of the inner surface or face of the cap—particularly, the ridges that are incorporated into the face of the cap—provide a stiff backing and cover to the proximal face of the flange 14. Because pressure and temperature rise rapidly inside the connector and attachments, the cap offers a stiff support to minimize distortion of parts (particularly the bonded shield 9) that are more susceptible to deformation during the harsh conditions of autoclaving.

Figure 11A:
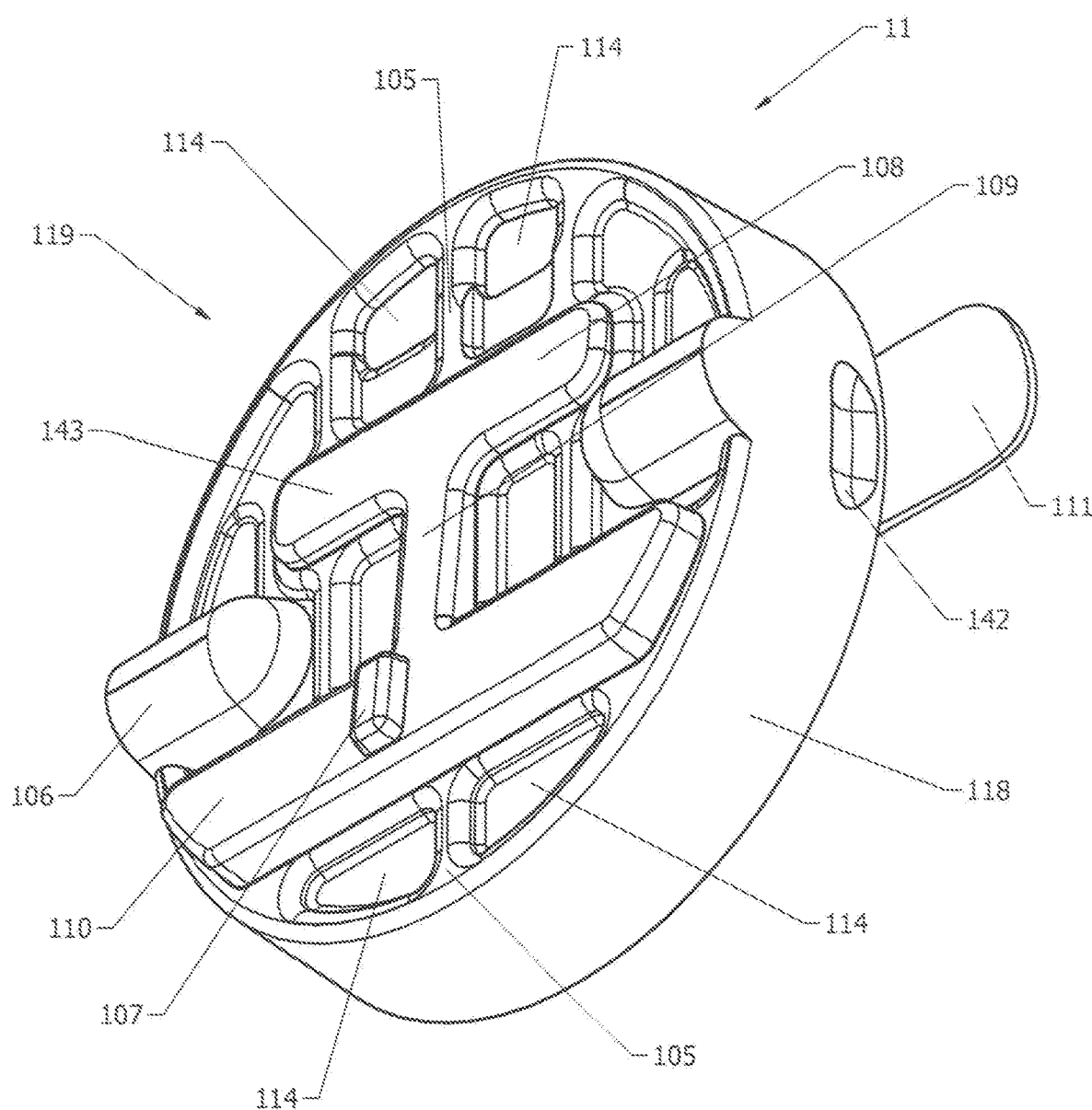
FIG. 11A is a perspective view of the protective cap, part of the view showing the exterior of the protective cap.
Figure 11B:
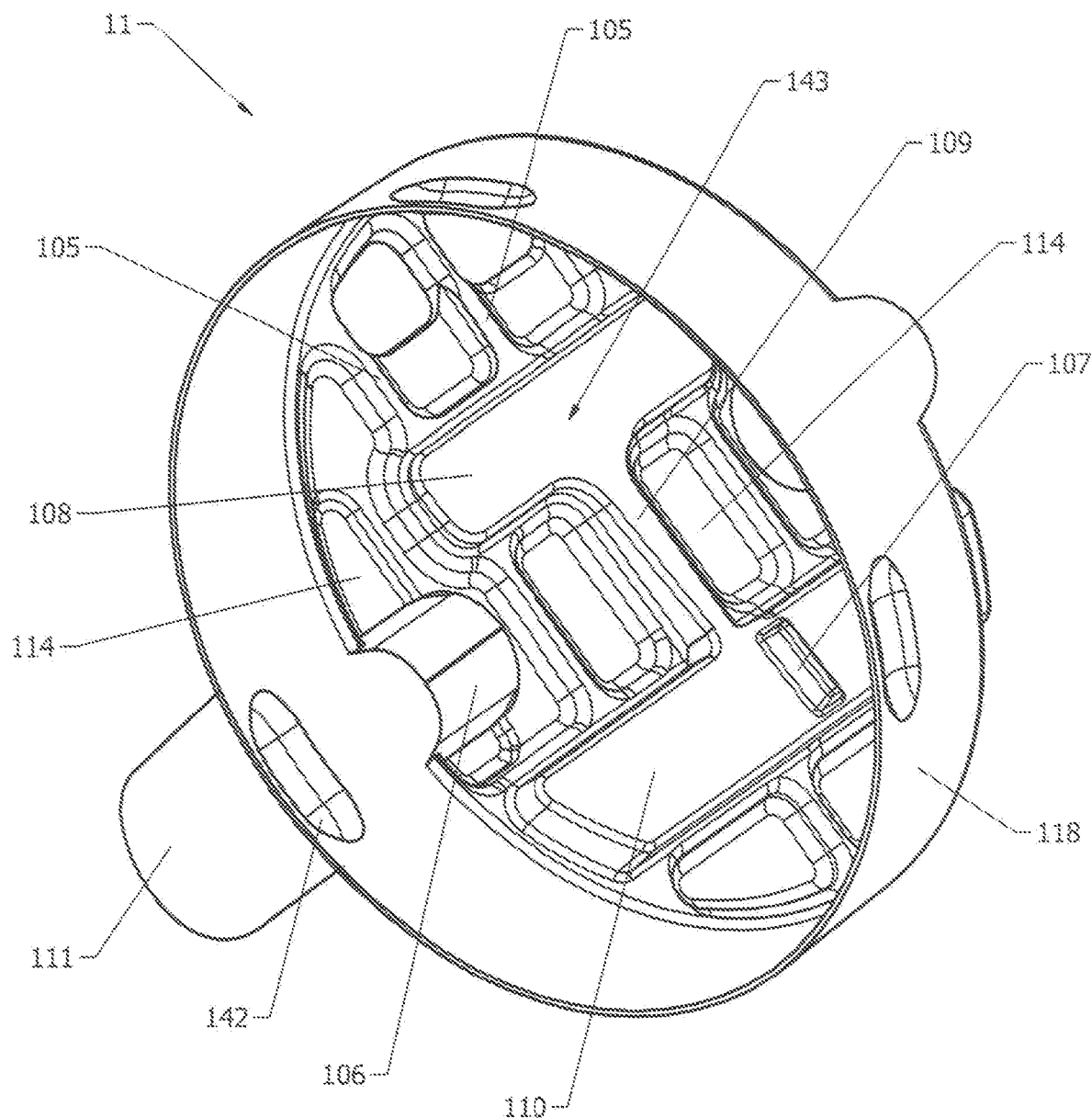
FIG. 11B is a perspective view of interior of protective cap part of the view showing the interior of the protective cap.
Figure 12:
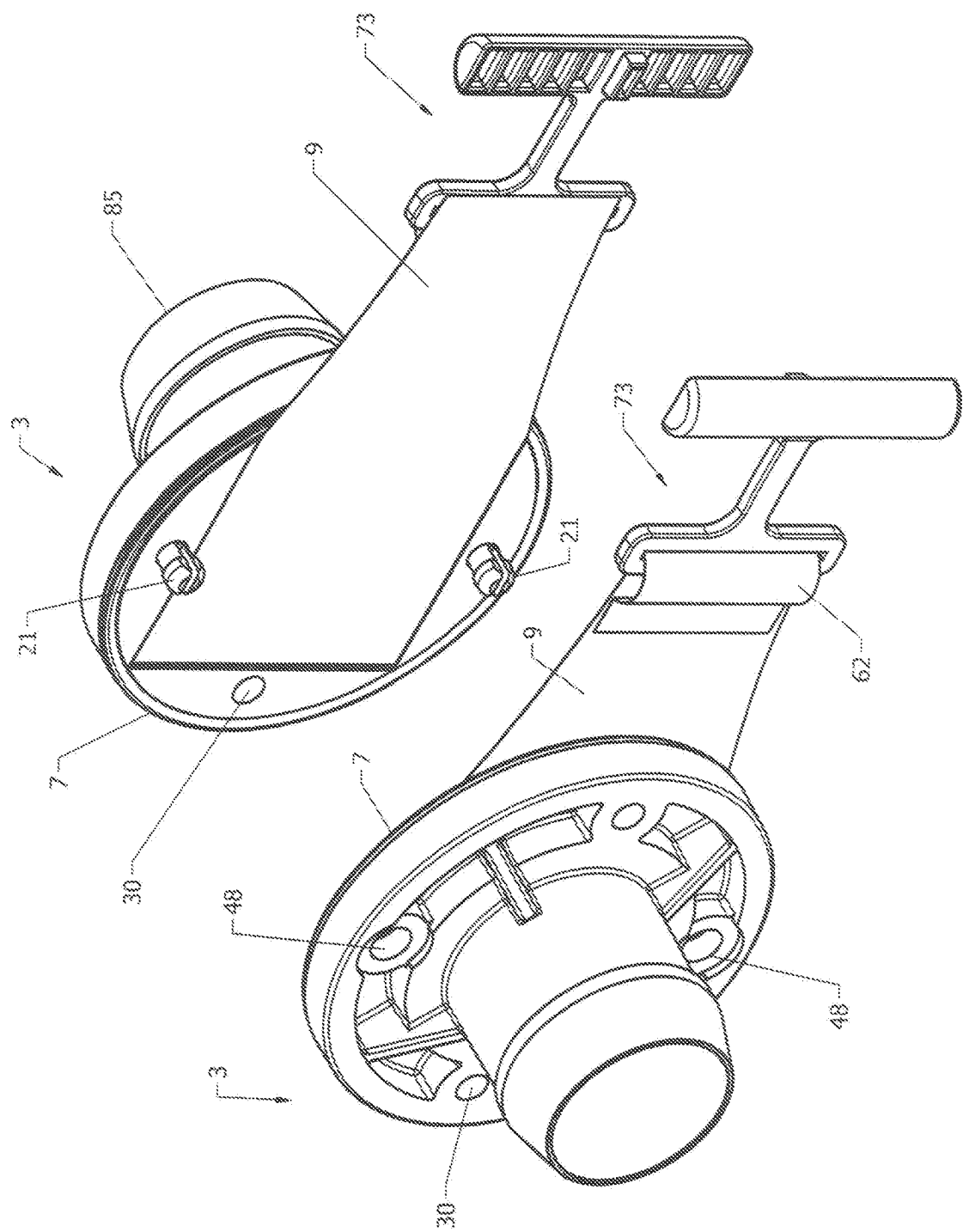
FIG. 12 is a perspective view of a pair of gendered connector components of the invention prior to being joined to each other.

The following pertinent parts of the cap are among those shown in FIGS. 11A and 11B: the cap flange 118, the cap cover top 119, ribs 105, river compartment 106, alignment post compartment 107, half pull grip engagement loop compartment 108, half pull grip stem compartment 109, half pull grip handle compartment 110, pull-off tab 111, and holes (a/k/a vents) 114.

Additional storage compartments can be incorporated into the cap. The larger the cap, the more room for such compartments.

While the ribs 105 provide stiffness, the holes 114 between ribs provide vent channels Those channels are important when the connector, attached to tubing or other components, is autoclaved. The presence of vent channels in the end cap 11 permits rapid venting across the porous shield. A completely flat cap pressed against the shield would inhibit venting.

There are a number of mechanisms to secure a cap against a flange. In the preferred embodiment, the sides of the cap extend, in a proximal-to-distal direction, beyond the distal surfaces of the flange. In that extended portion, inward protrusions 142 are formed that extend past the peripheral distal surface of the flange so that they can secure the cap against the flange using heat or other methods. The shape of such protrusions may be varied to achieve the desired gripping force and/or to facilitate the addition or removal of the cap from the flange connector. The same results may be achieved by other means. Material not folded over may be used to assist in the removal of the fold from the cap when required. Alternately, the side or any other part of the cap may be scored or notched to form a break or tear line for disassembling the cap for easy removal.

Method of Joining Two Connectors

This method is also an aspect of the invention.

The following steps are designed to achieve sterile joining of two conductors of the invention, although not necessarily in the order described.

1) Assemble the flange connectors are connect them to tubing, which in turn may be connected to other equipment.
2) Insert the rivet(s) into their respective hole(s) in the flange and secure them with an adhesive. An example of an adhesive that can be used is product 7937-v-vt from Tangent. Winsted, Conn. which is LED light curable)
3) Attach a half pull grip to the shield, bonding the shield to the recessed flange surface so it covers the connector tube and the inner O-ring. Once the shield is bonded to the recessed flange surface, fold back the fold-back segment of over the cover segment. A portion of the loop segment 62 of the shield is attached to the half pull grip (for example, by sliding it through slot 121), folded back, and secured to another portion of the loop segment 100.
4) Insert each half pull grip into its corresponding compartment in the end cap. Follow by adding the end cap and half pull grip to the face of the flange. Then attach and secure the protective cap to the flange of the connector (e.g., with a clip or protrusion element on the cap). The cap covers the entire proximal face of the connector 58, the shield, and the rivet.
5) Sterilize the assembled flange connector and the connected tubing in concert with a suitable device.
6) Bring the sterilized assembled connector is brought into convenient proximity with another sterilized assembled connector.
7) Remove the protective caps from the connectors and move the end of the shield attached to the pull grip as far as possible from the connector without breaking the bonding between the shield and the recessed flange surface. The folded segment of the shield is kept in the folded configuration. The proximal surfaces of the flanges of the two connectors are brought as close as possible together. Assure so that each half pull grip is mated with a pull grip from the facing connector. Insert each rivet head into an opposing hole on the other connector, the net result being that their shields contact each other and protrude in the same direction from the connectors.
8) Exert a pulling force on the pull grip so as to pull the protective shield out and away from the joined connectors.
9) Fill the remaining holes with fasteners that are tightened as needed to effect a good seal between the O-rings (and the V-rings).

What is claimed is:

1. A connector for facilitating a connection of one piece of tubing to another so that fluid can flow from one to the other in a sterile manner, said connector comprising a proximal end and a distal end, such that said connector comprises (1) a connector tube, (2) a flange at a proximal end of the connector tube and the proximal end of the connector, (3) a circular collar and (4) an O-gasket, said circular collar at the proximal end of the connector tube, said circular collar separating said flange from said connector tube so that there is a groove between said tube and said flange, the circular collar providing a distal end of the groove, said groove being an O-gasket groove capable of receiving an O-gasket, said O-gasket inserted into said groove at the proximal end of said connector, said O-gasket encircling the proximal end of the connector tube, and thereby possessing an outer perimeter, a portion of said O-gasket protruding from the flange so as to be capable of contact with an O-gasket of an identical connector when the two connectors are joined at their proximal ends, wherein the flange comprises a proximal surface, such that said proximal surface comprises a forward flange surface and a recessed flange surface, said recessed flange surface containing at least part of a removable protective shield attached to the recessed flange surface, said recessed flange surface comprising a central opening of diameter greater than an opening at the proximal end of the connector tube.

2. The connector of claim 1, wherein said forward flange surface comprises an inner edge, wherein the recessed flange surface is surrounded on three sides by recessed wall surfaces, each of said three wall surfaces extending from the recessed flange surface to the forward flange surface where each wall surface meets the inner edge of the forward flange surface and wherein the recessed flange surface comprises the central opening concentric with the connector tube.

3. The connector of claim 2, wherein said connector comprises fastener holes, wherein there is a distance between any two fastener holes, and wherein said connector comprises a central axis running in a proximal to distal direction through said tube, and wherein the fastener holes:
   a) are all centered at the same distance from the central axis of the connector tube;
   b) are equidistant from each other;
   c) are, as regards to the forward and recessed flange surfaces, either in both the forward flange surface and the recessed flange surface, entirely in the forward flange surface or entirely in the recessed flange surface;
   d) are, as regards to adjacent fastener holes, distributed such that the distance between at least one pair of adjacent fastener holes is large enough so that their respective fasteners, if in place, will not block removal of the shield;
   e) the fastener holes are as close as possible to the outer perimeter of the O-gasket groove without interfering with the attachment of the protective shield to the recessed flange surface and without preventing the shield from covering the recessed flange central opening and the O-gasket.

4. The connector of claim 2, wherein at least part of the removable protective shield comprises a shield cover segment and a foldable shield fold-back segment, said removable protective shield bonded to the recessed flange surface, the segment of the shield that is bonded being the shield cover segment, said shield cover segment at one end of the shield.

5. The connector of claim 4 wherein the shield is supplemented with a stiff, perforated partition sufficiently large to cover the shield cover segment, said partition bonded to the fold-back segment of said shield.

6. The connector of claim 5 wherein the partition is bonded at a position on the shield such that an edge of the partition is located along a fold in the shield when said shield is folded back on itself to an extent that does not result in breakage of any bonds between the shield and the recessed flange surface.

7. The connector of claim 5 wherein the partition is between the fold-back segment of the shield and the cover segment of the shield when said fold-back segment is folded back over the cover segment.

8. The connector of claim 1, said flange comprising fastener holes.

9. The connector of claim 8, wherein two or more fastener holes are fastener holes for rivets and each rivet fastener hole consists of three segments: a narrow segment; a middle segment; and a wide segment; wherein the segments progress from wide to narrow in the distal to proximal direction.

10. The connector of claim 8, wherein two or more fastener holes are fastener holes for bolts designed to accept nuts.

11. The connector of claim 8 where a number of fastener holes comprised by the flange is either four, six, or eight.

12. The connector of claim 1 wherein said connector comprises a central axis running in a proximal to distal direction through it, where the flange further comprises a groove for a V-gasket, such that as regards to the central axis of the connector tube, said V-gasket groove is concentric with, but more peripheral than the outer perimeter of the groove for the O-gasket.

13. A pair of connectors, wherein each connector in the pair is a connector for facilitating the connection of one piece of tubing to another so that fluid can flow from one to the other in a sterile manner, each said connector comprising a proximal end and a distal end,
   wherein each said connector comprises (1) a connector tube, (2) a flange at a proximal end of the connector tube and the proximal end of the connector, (3) a circular collar and (4) an O-gasket, said circular collar at the proximal end of the connector tube, the circular collar of each connector separating its flange from its connector tube so that there is a groove between said tube and said flange, the circular collar providing a distal end of the groove, said groove being an O-gasket groove capable of receiving an O-gasket, said O-gasket inserted into said groove at the proximal end of said connector, said O-gasket encircling the proximal end of the connector tube, and thereby possessing an outer perimeter, a portion of said O-gasket protruding from the flange so as to be in contact with the O-gasket of the other connector of the pair,
   wherein the flange of each connector comprises a proximal surface, such that said proximal surface comprises a forward flange surface and a recessed flange surface, where the recessed flange surface comprises a removable protective shield attached to the recessed flange surface, said recessed flange surface also comprising a central opening of diameter greater than an opening at the proximal end of the connector tube,
   wherein the connectors in the pair are joined to each other at their proximal ends.

14. The pair of connectors of claim 13, wherein each said forward flange surface comprises an inner edge, wherein the recessed flange surface of each connector is surrounded on three sides by recessed wall surfaces, wherein the said three wall surfaces of each connector extend from the recessed flange surface of said connector to the forward flange surface of said connector, where each wall surface meets the inner edge of the forward flange surface of said connector and wherein the recessed flange surface of each connector comprises the central openng concentric with its connector tube.

15. The pair of connectors of claim 14 wherein the flange of each connector comprises fastener holes, wherein there is a distance between any two fastener holes, and wherein each connector comprises a central axis running in a proximal to distal direction through the center of its connector tube, and wherein the fastener holes of each connector:
   a) are all centered at the same distance from the central axis of that connector tube;
   b) are equidistant from each other;
   c) are, as regards to the forward and recessed flange surfaces, either in both the forward flange surface and the recessed flange surface, entirely in the forward flange surface or entirely in the recessed flange surface;
   d) are, as regards to adjacent fastener holes, distributed such that the distance between at least one pair of adjacent fastener holes is large enough so that their respective fasteners, if in place, will not block removal of the shield;
   e) the radial distance from the central axis of the connector tube to the center of its fastener holes is minimized so that the fastener holes are as close as possible to the outer perimeter of the O-gasket groove.

16. The pair of connectors of claim 15, wherein two or more fastener holes of each connector are fastener holes for rivets and each rivet fastener hole consists of three segments: a narrow segment; a middle segment; and a wide segment; and wherein the segments progress from wide to narrow in the distal to proximal direction.

\* \* \* \* \*